US007355055B2

(12) United States Patent
Upadhyay et al.

(10) Patent No.: US 7,355,055 B2
(45) Date of Patent: Apr. 8, 2008

(54) COMPOUNDS FOR TREATMENT OF LIPASE-MEDIATED DISEASES

(75) Inventors: Shakti Upadhyay, Navi Mumbai (IN); Raman Yadav, Navi Mumbai (IN); Vijay Gangan, Navi Mumbai (IN); Yogesh Kanekar, Navi Mumbai (IN)

(73) Assignee: Reliance Life Sciences Pvt. Ltd., Maharashtra (IN)

( * ) Notice: Subject to any disclaimer, the term of this patent is extended or adjusted under 35 U.S.C. 154(b) by 99 days.

(21) Appl. No.: 11/222,901

(22) Filed: Sep. 8, 2005

(65) Prior Publication Data

US 2007/0054958 A1  Mar. 8, 2007

(30) Foreign Application Priority Data

Jul. 21, 2005  (IN)  ................... 864/2005

(51) Int. Cl.
*C07C 50/04* (2006.01)
*C07C 69/74* (2006.01)
*A01N 43/02* (2006.01)
(52) U.S. Cl. ........................... 552/293; 560/1; 514/449
(58) Field of Classification Search ................ 568/630; 552/293; 560/1; 514/449
See application file for complete search history.

(56) References Cited

U.S. PATENT DOCUMENTS 4,598,089 A   7/1986  Hadvary et al.

FOREIGN PATENT DOCUMENTS

WO   WO-2004/094393 A1   11/2004

OTHER PUBLICATIONS

Buchwald, H. et al. (Oct. 1980). "Long-Term, Continuous Intravenous Heparin Administration by an Implantable Infusion Pump in Ambulatory Patients with Recurrent Venous Thrombosis," *Surgery* 88(4):507-516.
Chappell, D. A. et al. (Jul. 8, 1994). "Cellular Catabolism of Normal Very Low Density Lipoproteins via the Low Density Lipoprotein Receptor-Related Protein/Alpha 2-Macroglobulin Receptor is Induced by the C-Terminal Domain of Lipoprotein Lipase," *The Journal of Biological Chemistry* 269(27):18001-18006.
Drent, M. L. et al. (Apr. 1993). "Lipase Inhibition: A Novel Concept in the Treatment of Obesity," *International Journal of Obesity and Related Metabolic Disorders* 17(4):241-244.
Dugi, K. A. et al. (Oct. 27, 1995). "Human Hepatic and Lipoprotein Lipase: The Loop Covering the Catalytic Site Mediates Lipase Substrate Specificity," *The Journal of Biological Chemistry* 270(43):25396-25401.
Faustinella, F. et al. (Aug. 18, 1992). "Functional Topology of a Surface Loop Shielding the Catalytic Center in Lipoprotein Lipase," *Biochemistry* 31(32):7219-7223.
Giller, T. et al. (Aug. 15, 1992). "Two Novel Human Pancreatic Lipase Related Proteins, hPLRP1 and hPLRP2 Differences in Colipase Dependence and in Lipase Activity," *The Journal of Biological Chemistry* 267(23):16509-16516.
Goldberg, I. J. et al. (Dec. 1982). "Lipoprotein Metabolism During Acute Inhibition of Hepatic Triglyceride Lipase in the Cynomolgus Monkey," *The Journal of Clinical Investigation* 70(6):1184-1192.
Goldberg, I. J. et al. (Feb. 1988), "Lipoprotein Metabolism During Acute Inhibition of Lipoprotein Lipase in the Cynomolgus Monkey," *The Journal of Clinical Investigation* 81(2):561-568.
Gupta, S. et al. (1989). "Effects of Embelin, an Antifertility Agent, on the Lipid Metabolism of Male Albino Rats," *Fitoterapia* 60(4):331-338.
Hide, W. A. et al. (Feb. 1992). "Structure and Evolution of the Lipase Superfamily," *Journal of Lipid Research* 33(2):167-178.
Higuchi, T. et al. (Sep. 10, 1974). "Pro-Drugs as Novel Drug Delivery Systems," *A.C.S. Symposium Series* 14 and In (1987) *Bioreversible Carriers in Drug Design*. Edward B. Roche ed., American Pharmaceutical Association Pergamon Press: Elmsford, NY., 7 pages. (Table of Contents).
Hixenbaugh, E. A. et al. (Mar. 5, 1989). "Hepatic Lipase in the Rat Ovary," *The Journal of Biological Chemistry* 264(7):4222-4230.
Jaye, M. et al. (Apr. 1999). "A Novel Endothelial-Derived Lipase That Modulates HDL Metabolism," *National Genetics* 21(4):424-428.
Krapp, A. et al. (May 1996). "Hepatic Lipase Mediates the Uptake of Chylomicrons and Beta-VLDL into Cells via the LDL Receptor-Related Protein (LRP)," *Journal of Lipid Research* 37(5):926-936.
Langer, R. (Sep. 28, 1990). "New Methods of Drug Delivery," *Science* 249(4976):1527-1533.
Langer, R. et al. (1983). "Chemical and Physical Structure of Polymers as Carriers for Controlled Release of Bioactive Agents: A Review," *Journal of Macromolecular Science Reviews in Macromolecular Chemistry and Physics* C23(1):61-126.
Langer, R. S. and Wise, D. L. eds. (1984). Medical Applications of Controlled Release vol. I Classes of Systems. CRC Press, Inc.: Boca Raton, FL., 4 pages. (Table of Contents).
Liu, M. S. et al. (Apr. 15, 1994). "Alteration of Lipid Profiles in Plasma of Transgenic Mice Expressing Human Lipoprotein Lipase," *The Journal of Biological Chemistry* 269(15):11417-11424.
Lowe, M. E. (Apr. 1997). "Molecular Mechanisms of Rat and Human Pancreatic Triglyceride Lipases," *The Journal Nutrition* 127(4):549-557.

(Continued)

*Primary Examiner*—Yvonne Eyler
*Assistant Examiner*—Lalitha Nagubandi
(74) *Attorney, Agent, or Firm*—Morrison & Foerster LLP

(57) ABSTRACT

Novel benzoquinone-derived compounds and polymorphs, prodrugs, geometric or optical isomers thereof, and pharmaceutically acceptable esters, ethers, carbamates, oximes of such compounds, polymorphs, prodrugs and isomers are provided. Process for preparation of compounds of the invention and pharmaceutical compositions containing such compounds and their use for reducing or inhibiting activity of lipase gene family for treatment, amelioration or prevention of lipase gene family mediated diseases and conditions including overweight, obesity, hyperlipidemia, hypercholesterolemia, hypertriglyceridemia, pancreatitis, diabetes, atherosclerosis, other cardiovascular diseases, metabolic syndromes, and metabolic disorders are provided. Methods of use of the compounds for skin care, hair care and cosmetics are provided.

12 Claims, No Drawings

OTHER PUBLICATIONS

Ma, Y. et al. (Nov. 1994). "Mutagenesis in Four Candidate Heparin Binding Regions (Residues 279-282, 291-304, 390-393, and 439-448) and Identification of Residues Affecting Heparin Binding of Human Lipoprotein Lipase," *Journal of Lipid Research* 35(11):2049-2059.

Mead, J. R. et al. (1999). "Lipoprotein Lipase, A Key Role in Atherosclerosis?" *Federation of European Biochemical Societies Letters* 462:1-6.

Nikolovska-Coleska, Z. et al. (May 6, 2004). "Discovery of Embelin as a Cell-Permeable, Small-Molecular Weight Inhibitor of XIAP Through Structure-Based Computational Screening of a Traditional Herbal Medicine Three-Dimensional Structure Database," *Journal of Medicinal Chemistry* 47(10):2430-2440.

Nykjaer, A. et al. (Jul. 15, 1993). "The Alpha 2-Macroglobulin Receptor/Low Density Lipoprotein Receptor-Related Protein Binds Lipoprotein Lipase and Beta-Migrating Very Low Density Lipoprotein Associated with the Lipase," *The Journal of Biological Chemistry* 268(20):15048-15055.

Olivecrona, G. et al. (1995). "Triglyceride Lipases and Atherosclerosis," *Current Opinions Lipidology* 6(5):291-305.

Olivecrona, T. et al. (1993). "Lipoprotein Lipase and Hepatic Lipase," *Current Opinions in Lipidology* 4(2):187-196.

Ranganathan, G. et al. (Mar. 31, 1995). "Tissue-Specific Expression of Human Lipoprotein Lipase," *The Journal of Biological Chemistry* 270(13):7149-7155.

Saudek, C. D. et al. (Aug. 31, 1989). "A Preliminary Trial of the Programmable Implantable Medication System for Insulin Delivery," *The New England Journal of Medicine* 321(9):574-579.

Sefton, M. V. (1987). "Implantable Pumps," *CRC Critical Reviews in Biomedical Engineering* 14(3):201-240.

Shimada, M. et al. (Aug. 25, 1993). "Overexpression of Human Lipoprotein Lipase in Transgenic Mice," *The Journal of Biological Chemistry* 268(24):17924-17929.

Smolen, V. F. and Ball, L. eds. (1984). *Controlled Drug Bioavailability* vol. 1 and 2. John Wiley & Sons, Inc.: New York, NY., 9 Pages. (Table of Contents).

van Tilbeurgh, H. et al. (Feb. 11, 1994). "Lipoprotein Lipase," *The Journal of Biological Chemistry* 269(6):4626-4633.

Verger, R. (1984). "Pancreatic Lipases"*In Lipases*. Bengt Borgström and Howard L. Brockman eds., Elsevier Science Publishers B.V.: Amsterdam, The Netherlands, pp. 83-150.

Winkler, F. K. et al. (Feb. 22, 1990). "Structure of Human Pancreatic Lipase," *Nature* 343(6260):771-774.

Winkler, U. K. et al. (Jun. 1979). "Glycogen, Hyaluronate, and Some Other Polysaccharides Greatly Enhance the Formation of Exolipase by *Serratia marcescens*," *Journal of Bacteriology* 138(3):663-670.

Wong, H. et al. (Dec. 15, 1991). "Domain Exchange: Characterization of a Chimeric Lipase of Hepatic Lipase and Lipoprotein Lipase," *Proceedings of the National Academy of Sciences of the United States of America* 88(24):11290-11294.

Wong, H. et al. (Jul. 2002). "The Lipase Gene Family," *Journal of Lipid Research* 43(7):993-999.

Yadav, R. P. et al. (Dec. 1998). "Purification and Characterization of a Regiospecific Lipase from *Aspergillus terreus*," *Biotechnology and Applied Biochemistry* 28(3):243-249.

COMPOUNDS FOR TREATMENT OF LIPASE-MEDIATED DISEASES

TECHNICAL FIELD OF THE INVENTION

The present invention relates to diseases and conditions mediated by genes of the lipase family. In particular, the invention relates to novel benzoquinone-derived compounds that affect the activity of lipase gene family enzymes.

BACKGROUND OF THE INVENTION

In many developed and developing countries, the trend towards adoption of a diet containing high fat content and low fiber concentrations continues to be on the rise, accompanied by a labor-unintensive sedentary lifestyle. Such excessive intake of fat, accompanied by reduced conversion of fat into energy because of sedentary lifestyles can lead to accumulation of fat in the body at various levels including body fluids, cells and tissues. Consequently there is a steady rise in a population at a heightened risk of metabolic disorders such as overweight or obesity, which progresses to associated disorders like diabetes, cardiovascular disorders, metabolic syndrome, and hypertension.

In general the first line of treatment for individuals suffering from such metabolic disorders, in particular overweight or obesity, involves adoption of a diet low in fat and regular exercise. Compliance with such regimen however can be poor and, as the disease progresses, treatment with therapeutic drugs becomes necessary.

Accordingly, studies have been made towards developing drugs that are safe and effective for prevention and treatment of clinical manifestations that are caused as a consequence of accumulation of fat in body fluids, cells and tissues. Thus, there is a continuing necessity for decreasing the absorption and accumulation of fat in the body in some manner.

One approach to prevent or reduce fat accumulation is by reducing or inhibiting agents that aid in digestion and absorption of fat at various levels in the body. Enzymes belonging to the lipase gene family are of the central importance in lipid metabolism, absorption and transportation.

Hepatic lipase and lipoprotein lipase are multifunctional proteins which mediate the binding, uptake, catabolism, and remodeling of lipoproteins and phospholipids. Lipoprotein lipase and hepatic lipase function while bound to the luminal surface of endothelial cells in peripheral tissues and the liver respectively. Both enzymes participate in reverse cholesterol transport, which is the movement of cholesterol from peripheral tissues to the liver either for excretion from the body or for recycling. Genetic defects in both hepatic lipase and lipoprotein lipase are known to be the cause of familial disorders of lipoprotein metabolism. Defects in the metabolism of lipoproteins result in serious metabolic disorders, including hypercholesterolemia, hyperlipidemia, and atherosclerosis.

The lipase gene family enzymes are involved in a wide array of metabolic pathways, ranging from lipid digestion, absorption, fatty acid uptake, lipoprotein transportation and also in inflammation (Wong Howard et al., 2002, The lipase gene family, Journal of Lipid Research, Vol. 43: 993-999).

Pancreatic lipase is one of the key enzymes in lipid metabolism. It is synthesized by pancreatic acinar cells where it is secreted into the intestinal lumen and aids in the intestinal absorption of long chain triglyceride fatty acids (Verger, R. 1984, Pancreatic Lipases In Lipases. B. Borgström and H. L. Brockman, editors. Elsevier, New York. 83-150; Lowe, M. E. 1997, Molecular mechanisms of rat and human pancreatic triglyceride lipases. J. Nutr. 127: 549-557).

The action of the triacylglycerol lipases is believed to be antiatherogenic because these enzymes lower serum triacylglycerol levels and promote HDL formation. (Olivecrona, G., and Olivecrona, T. (1995) Curr. Opin. Lipid. 6:291-305). Lipoprotein lipase is the major enzyme responsible for the distribution and utilization of triglycerides in the body. Lipoprotein lipase hydrolyzes triglycerides in both chylomicrons and VLDL. Hepatic lipase hydrolyzes triglycerides in IDL and HDL, and is responsible for lipoprotein remodeling. Hepatic lipase also functions as a phospholipase, and hydrolyzes phospholipids in HDL.

Lipase members function in the metabolism of circulating lipoproteins. Hepatic lipase plays a role in the uptake of HDL cholesterol (Olivecrona, T., et al. 1993, Lipoprotein lipase and hepatic lipase. Curr. Opin. Lipidol. 4: 187-196). It is synthesized exclusively in the liver, where it is predominantly found (Hixenbaugh, E. A, et al., 1989, Hepatic lipase in the rat ovary. J. Biol. Chem. 264: 4222-4230).

A third member of the lipase gene family, lipoprotein lipase (LPL), is distributed in a variety of tissues, with the highest concentrations occurring in adipose tissue and muscle. This lipase is bound to capillary endothelium, where it functions to supply the underlying tissue with fatty acids derived from the triglyceride-rich core of circulating chylomicrons and VLDL (Olivecrona, T., and G. Bengtsson-Olivecrona. 1993. Lipoprotein lipase and hepatic lipase. Curr. Opin. Lipidol. 4: 187-196). In the process, LPL transforms these lipoproteins into remnant and HDL particles. Accumulating evidence suggest that LPL produced by macrophages in the vascular wall may facilitate the development of atherosclerosis by promoting lipid accumulation within the lesion. LPL has been shown to be involved in the pathogenesis of atherosclerosis (Mead J R, et al. 1999, "Lipoprotein Lipase, a key role in atherosclerosis?" FEBS Lett., November 26, 462(1-2): 1-6). Several groups have also proposed that both LPL and hepatic lipase besides their traditional role as lipolytic enzyme also appear to serve as ligands in the metabolism of plasma lipoproteins (Nykjaer, A., et al., 1993, The alpha 2-macroglobulin receptor/low density lipoprotein receptor-related protein binds lipoprotein lipase and beta-migrating very low density lipoprotein associated with the lipase. J. Biol. Chem. 268: 15048-15055; Krapp, A., S. et al., 1996. Hepatic lipase mediates the uptake of chylomicrons and VLDL into cells via the LDL receptor-related protein (LRP). J. Lipid Res. 37: 926-936). Transgenic animals expressing human lipoprotein lipase or hepatic lipase have decreased levels of plasma triglycerides and an increased level of high density lipoprotein (HDL) (Shimada, M., et al (1993) J. Biol. Chem. 268:17924-17929; Liu, M.-S., et al. (1994) J. Biol. Chem. 269:11417-11424).

A more recently discovered member of the lipase gene family is endothelial lipase. The function of this lipase is though uncertain at this time, it is believed to have a role in HDL metabolism (Jaye, M., et al., 1999, A novel endothelial-derived lipase that modulates HDL metabolism. Nat. Genet. 21: 424-428).

With the increasingly recognized potential of lipases in fat metabolism pathway, the drugs that inhibit or reduce the activity of lipases at various levels in the body form the front line of therapy for the treatment of diseases mediated by accumulation of fat at elevated levels.

A lipase inhibitor that is marketed as anti-obesity drug include Orlistat (XENICAL®) is described in U.S. Pat. No. 4,598,089. European Patent Application No. EP129748, relates to Orlistat and related compounds and their use in inhibiting pancreatic lipase and treating hyperlipidemia and obesity. Orlistat inhibits only intestinal lipases such as gastric, pancreatic and carboxylester lipases, particularly pancreatic lipase, in the gut lumen and blocks the digestion of dietary fat by preventing lipase from interacting with its lipid target. It however does not appear to have an effect on lipases other than the intestinal lipases, such as hepatic lipase or endothelial lipase, which are also recognized as having roles in catalyzing the hydrolysis of lipids. (Drent M L, van der Veen E A. Lipase inhibition: A novel concept in the treatment of obesity. Int J. Obes. Relat. Metab. Disord. 1993; 17:241-244.) Orlistat also tends to produce a high incidence of unpleasant (relatively harmless) side effects such as diarrhea.

Compounds that inhibit hepatic lipase and/or endothelial lipase activity have been disclosed in PCT Application No. WO2004094393 for the treatment of hepatic and/or endothelial lipase mediated diseases. The compounds are primarily directed towards increasing HDL levels by inhibiting the activity of hepatic and/or endothelial lipase, and are not intended to target intestinal or other lipases.

Therefore, it is desirable to develop new compounds that are useful in reducing or inhibiting metabolism, absorption, and accumulation of fat at various levels including fluids, cells, and tissues in the body by inhibiting or reducing the activity of all members of lipase gene family of interest and not just a particular type of lipase.

A plant benzoquinone embelin (2,5-dihydroxy-3-undecyl-1,4-benzoquinone) obtained from the dried fruit of *Embelia ribes* and known as an antifertility agent has also been reported to elevate activities of the lipogenic enzymes, malate dehydrogenase, glucose-6-phosphate dehydrogenase and hydroxymethylglutaryl-CoA reductase while essentially not affecting lipolytic enzyme activities. (Gupta S. et al., Fitoterapia 60(4):331-338 (1989).) Embelin is also used as ateniacide, as having antitumor, anti-inflammatory and analgesic properties (Chitra et al. Chemotherapy 40:109 (1994)) and as a cell-permeable, non-peptide inhibitor of X-linked inhibitor of apoptosis (XIAP). (Nikolovska-Coleska et al. J. Med. Chem. 47:2430 (2004)).

SUMMARY OF THE INVENTION

The present invention provides compounds of Formula (I):

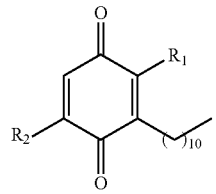

wherein:

$R_1$ and $R_2$ are each independently selected from the group consisting of hydrogen, $C_3$-$C_{13}$ alkyl, $C_1$-$C_{20}$ haloalkyl, $C_2$-$C_{13}$ alkenyl, $C_2$-$C_{13}$ alkynyl, $C_4$-$C_6$ cycloalkyl, $C_4$-$C_6$ cycloalkenyl, $C_1$-$C_{13}$ alkoxyalkyl, $C_1$-$C_5$ alkylcycloalkyl, $C_1$-$C_5$ alkylcycloalkenyl, $C_1$-$C_{13}$ alkylamine, $C_1$-$C_{13}$ arylamine, $C(O)C_1$-$C_6$ alkyl, O—$C(O)C_1$-$C_6$ alkyl, heterocycloalkyl, aryl, alkylaryl, C(O)aryl and O—C(O)aryl; wherein each of the foregoing groups may optionally bear 1 to 6 substituents independently selected from hydrogen, halo, nitro, amino, cyano, isocyano, thio, $C_1$-$C_6$ alkyl, cycloalkyl, aryl, alkoxy, and aryloxy groups. However in accordance with the present invention $R_1$ and $R_2$ are not methyl, methoxy, ethyl, ethoxy, phenyl, and hydroxy.

The present invention also relates to the compounds of formula (I) and derivatives thereof including but not limited to polymorphs, isomers and prodrugs thereof, geometric or optical isomers thereof, and pharmaceutically acceptable esters, ethers, carbamates of such compounds, all solvates and hydrates thereof and all salts thereof.

In another aspect present invention provides use of compounds of formula (I) in reducing or inhibiting metabolism, absorption, and accumulation of fat at various levels including fluid, cellular, and tissue levels in body by inhibiting or reducing the activity of enzymes belonging to lipase gene family.

In another embodiment, the invention provides compounds of formula (II):

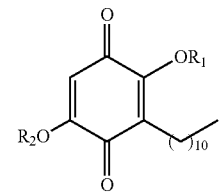

wherein:

$R_1$ and $R_2$ are each independently selected from the group consisting of $C_3$-$C_{13}$ alkyl, $C_1$-$C_{20}$ haloalkyl, $C_2$-$C_{13}$ alkenyl, $C_2$-$C_{13}$ alkynyl, $C_4$-$C_6$ cycloalkyl, $C_4$-$C_6$ cycloalkenyl, $C_1$-$C_{13}$ alkoxyalkyl, $C_1$-$C_5$ alkylcycloalkyl, $C_1$-$C_5$ alkylcycloalkenyl, $C_1$-$C_{13}$ alkylamine, $C_1$-$C_{13}$ arylamine, $C(O)C_1$-$C_6$ alkyl, heterocycloalkyl, aryl, alkylaryl, and C(O)aryl; wherein each of the foregoing groups may optionally bear 1 to 6 substituents independently selected from hydrogen, halo, nitro, amino, cyano, isocyano, thio, $C_1$-$C_6$ alkyl, cycloalkyl, aryl, alkoxy, and aryloxy groups. However in accordance with the present invention $R_1$ and $R_2$ are not methyl, ethyl, and phenyl.

The present invention also relates to the compounds of formula (II) and derivatives thereof including but not limited to polymorphs, isomers and prodrugs thereof, geometric or optical isomers thereof, and pharmaceutically acceptable esters, ethers, carbamates of such compounds, all solvates and hydrates thereof and all salts thereof.

In another aspect present invention provides use of compounds of formula (II) in reducing or inhibiting metabolism, absorption, and accumulation of fat at various levels including fluid, cellular, and tissue levels in body by inhibiting or reducing the activity of enzymes belonging to lipase gene family.

In another embodiment, the invention provides compounds of formula (III):

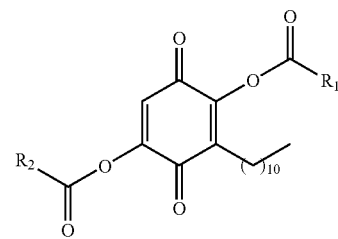

wherein:

$R_1$ and $R_2$ are each independently selected from the group consisting of hydrogen, $C_1$-$C_{13}$ alkyl, $C_1$-$C_{20}$ haloalkyl, $C_2$-$C_{13}$ alkenyl, $C_2$-$C_{13}$ alkynyl, $C_4$-$C_6$ cycloalkyl, $C_4$-$C_6$ cycloalkenyl, $C_1$-$C_{13}$ alkoxyalkyl, $C_1$-$C_{13}$ alkylamine, $C_1$-$C_{13}$ arylamine, $C_1$-$C_5$ alkylcycloalkyl, $C_1$-$C_5$ alkylcycloalkenyl, $C(O)C_1$-$C_6$ alkyl, heterocycloalkyl, aryl, alkylaryl, and $C(O)$aryl; wherein each of the foregoing groups may optionally bear 1 to 6 substituents independently selected from hydrogen, halo, nitro, amino, cyano, isocyano, thio, $C_1$-$C_6$ alkyl, cycloalkyl, aryl, alkoxy, and aryloxy groups.

The present invention also relates to the compounds of formula (III) and derivatives thereof including but not limited to polymorphs, isomers and prodrugs thereof, geometric or optical isomers thereof, and pharmaceutically acceptable esters, ethers, carbamates of such compounds, all solvates and hydrates thereof and all salts thereof.

In another aspect present invention provides use of compounds of formula (III) in reducing or inhibiting metabolism, absorption, and accumulation of fat at various levels including fluid, cellular, and tissue levels in body by inhibiting or reducing the activity of enzymes belonging to lipase gene family.

The present invention further provides the process for preparation of compounds of formulas (I), (II) and (III) and derivatives thereof.

The present invention provides a pharmaceutical compositions comprising any of the compounds of this invention including their polymorph, prodrug, isomer or pharmaceutically acceptable ester, ethers, carbamate, and oximes useful in reducing or inhibiting activity of enzymes of lipase gene family participating in metabolism, absorption, and accumulation of lipids in body at various levels including body fluid, cellular and tissue level for treatment, amelioration or prevention of diseases mediated by lipase gene family enzyme including but not limited to overweight or obesity, hyperlipidemia, hypercholesterolemia, hypertriglyceridemia, pancreatitis, hyperglycemia, atherosclerosis, metabolic syndromes, other cardiovascular diseases, and other metabolic disorders.

The present invention in further aspect also provides the use of compounds of formulas (I), (II) and (III) and derivatives thereof for skin, hair care or cosmetic preparation.

The present invention in still further aspect provides the use of compounds of formulas (I), (II) and (III) and derivatives thereof to prevent or treat cellular and tissue damage caused by microbial pathogens secreting lipases.

The present invention also relates to the pharmaceutical formulations comprising of any of compound of formulas (I), (II) and (III) and derivatives thereof by themselves or in conjunction with a suitable pharmaceutically acceptable excipient. Such formulations are useful in reducing or inhibiting activity of enzymes of lipase gene family participating in metabolism, absorption, and accumulation of lipids in body at various levels including body fluid, cellular and tissue level for treatment, amelioration or prevention of diseases mediated by lipase gene family enzymes such as overweight or obesity, hyperlipidemia, hypercholesterolemia, hypertriglyceridemia, pancreatitis, diabetes, atherosclerosis, other cardiovascular diseases, metabolic syndromes, and metabolic disorders.

The present invention also provides the manner of manufacture of medicaments comprising of compounds of formulas (I), (II) and (III) and derivatives thereof in a therapeutically effective amount either alone or in combination with pharmaceutically acceptable adjuvant. The compounds of formulas (I), (II) and (III) and derivatives thereof may further be combined with other active ingredients.

The present invention further relates to the method of treatment of diseases mediated by lipase gene family of enzymes by administering in a therapeutically effective amount any compound of formulas (I), (II) and (III) and derivatives thereof in human or animal subjects.

The present invention and other objects, features, and advantages of the present invention will become further apparent in the following Detailed Description of the Invention and the accompanying embodiments.

DETAILED DESCRIPTION OF THE INVENTION

The present invention provides novel methods and compositions for use in reducing or inhibiting activity of lipase gene family enzymes for treatment, amelioration or prevention of lipase gene family enzyme mediated diseases and conditions in an individual.

Definitions

Unless otherwise specified the following definitions are set forth to illustrate and define the meaning and scope of the various terms used to describe the invention herein.

The term "lipase gene family enzymes" as used herein include but are not limited to hepatic lipase; intestinal lipases including gastric lipase, pancreatic lipase, and carboxylester lipase; endothelial lipase; phospholipase and other related lipases.

The term "pharmaceutically acceptable" as used herein refers to the substance including carrier, diluent, vehicle excipient, or composition being compatible chemically and/or toxicologically, with the other ingredients comprising a formulation that is not deleterious to the recipient thereof.

The term "alkyl" by itself or as part of another substituent means, unless otherwise defined, a straight or branched chain monovalent hydrocarbon radical, such as for example, methyl, ethyl, n-propyl, isopropyl, n-butyl, tertiary butyl, sec-butyl, n-pentyl and n-hexyl.

The term, "alkenyl" employed alone or in combination with other terms means a straight chain or branched monovalent hydrocarbon group having the stated number ranges of carbon atoms, and groups such as vinyl, propenyl, crotonyl, isopentenyl, and various butenyl isomers.

The term, "alkynyl" employed alone or in combination with other terms means a straight chain or branched acyclic carbon chain which contains a carbon-to-carbon triple bond hydrocarbon group having the stated number ranges of carbon atoms, and groups.

The term "cycloalkyl" means a cyclic either monocyclic or polycyclic alkyl radical having at least 3 carbon atoms and typically 3 to 7 carbon atoms. Examples are: cyclopropyl, cyclobutyl, cyclopentyl, cyclohexyl or cycloheptyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, 2° butoxy and 3° butoxy, or 2-methoxyethoxy.

The term "$C_1$ to $C_5$ alkylcycloalkyl" means any of the $C_1$ to $C_5$ alkyl group is substituted on the cycloalkyl group and the composite group is attached to the nucleus at the alkyl terminus.

The term "$C_1$ to $C_6$ heterocycloalkyl" means a heterocycloalkyl group having 2-6 carbon atoms, preferably 3-5 carbon atoms, and including at least one heteroatom selected from N, O and/or S, which may be attached via a heteroatom or a carbon atom.

The term "aryl" means an aromatic hydrocarbon group having a single (e.g. phenyl) or a fused ring system (e.g. naphthalene, anthracene, phenanthrene, etc.). A typical aryl group is aromatic carbocylic ring having 6, 7, 8, 9 or 10 carbon atoms, such as phenyl, naphthyl, tetrahydronaphthyl or indenyl, which may optionally be substituted with one or more substituents selected from hydroxy, amino, halogen, nitro, cyano, $C_1$ to $C_4$ alkyl, $C_2$ to $C_4$ alkenyl, $C_2$ to $C_4$ alkynyl, $C_1$ to $C_4$ alkoxy, $C_1$ to $C_4$ dialkylamino, the alkyl moieties having the same meaning as previously defined. The preferred aromatic hydrocarbon group is phenyl.

The term "$C_3$ to $C_9$ heteroaryl" means a substituted or unsubstituted aromatic group having 3, 4, 5, 6, 7, 8 or 9 carbon atoms, at least including one heteroatom selected from N, O and/or S, like imidazolyl, thiadiazolyl, pyridyl, (benzo)thienyl, (benzo)furyl, quinolyl, tetrahydroquinolyl, quinoxalyl or indolyl. The substituents on the heteroaryl group may be selected from the group of substituents listed for the aryl group. The heteroaryl group may be attached via a carbon atom or a heteroatom, if feasible.

The term "$C_6$ to $C_{10}$ aryloxy" means an aryl group containing 6, 7, 8, 9, or 10 carbon atoms as defined previously, attached to an oxygen atom. $C_3$ to $C_9$ heteroaryloxy groups are analogs of the $C_6$ to $C_{10}$ aryloxy groups, at least including one heteroatom selected from N, O or S.

The term "halo" means fluoro, chloro, bromo, or iodo.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substitutents together forming a ring, such as, for example, —$NH_2$, methylamino, ethylamino, dimethylamino, diethylamino, methyl-ethylamino, pyrrolidin-1-yl or piperidino etc., preferably amino, dimethylamino and diethylamino and particularly preferred primary amino.

The term "cyano," alone or in combination, signifies a —CN group.

The term "nitro," alone or in combination, signifies a —$NO_2$ group.

The term "heterocyclic group" refers to radicals or groups derived from monocyclic or polycyclic saturated or unsaturated, substituted or unsubstituted heterocyclic nuclei having 5, 6, 7, 8, 9, 10, 11, 12, 13 or 14 ring atoms and containing 1, 2 to 3 hetero atoms selected from the group consisting of nitrogen, oxygen or sulfur.

The term substituent is "non-interfering" substituents. By "non-interfering" is meant that the group is suitable chemically and stability wise to occupy the designated position and perform the designated or intended role. Thus unsuitable groups are excluded from the definition of "non-interfering".

In addition, compounds of Formula (I) and derivatives thereof may be labeled with an isotope (e.g., $^3H$, $^{14}C$, $^{35}S$, $^{125}I$, etc.).

A "prodrug" refers to a compounds capable of being converted to compounds of the present invention by reactions of an enzyme, gastric juice, or the like, under physiological conditions in vivo, specifically compounds capable of being converted to compounds of the present invention upon enzymatic oxidation, reduction, hydrolysis, or the like, or a compounds capable of being converted to compounds of the present invention upon hydrolysis or the like by gastric juice or the like.

A "polymorph" refers to a compound that occurs in two or more forms.

The phrase "therapeutically effective amount" means an amount of a compound of the present invention that—treat or prevent the particular disease, condition, or disorder; or attenuates, ameliorates, or eliminates one or more symptoms of the particular disease, condition, or disorder; or prevents o delays the onset of one or more symptoms of the particular disease, condition, or disorder described herein.

The use of terms $C_1$-$C_n$ is used to signify each of $C_1$, $C_2$, $C_3$, ... $C_n$. Thus, $C_1$-$C_{20}$ includes $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, and $C_{20}$. $C_1$-$C_{13}$ includes each of $C_1$, $C_2$, $C_3$, $C_4$, $C_5$, $C_6$, $C_7$, $C_8$, $C_9$, $C_{10}$, $C_{11}$, $C_{12}$, $C_{13}$. $C_2$-$C_{13}$ includes each of $C_2$, $C_3$, $C_4$, $C_5$, $C_6$, $C_7$, $C_8$, $C_9$, $C_{10}$, $C_{11}$, $C_{12}$, $C_{13}$, and so forth.

Lipases

Three members of the human triacylglycerol lipase family have been described: pancreatic lipase, lipoprotein lipase, and hepatic lipase (Goldberg, I. J., Le, N.-A., Ginsberg, H. N., Krauss, R. M., and Lindgren, F. T. (1988) J. Clin. Invest. 81,561-568; Goldberg, I. J., Le, N., Patemiti J. R., Ginsberg, H. N., Lindgren, F. T., and Brown, W. V. (1982) J. Clin. Invest. 70,1184-1192; Hide, W. A., Chan, L., and Li, W.-H. (1992) J. Lipid. Res. 33,167-178). Pancreatic lipase is primarily responsible for the hydrolysis of dietary lipids. Variants of pancreatic lipase have been described, but their physiological role has not been determined (Giller, T., Buchwald, P., Blum-Kaelin, D., and Hunziker, W. (1992) J. Biol. Chem. 267,16509-16516).

The lipase polypeptides encoded by these lipase genes are approximately 450 amino acids in length with leader signal peptides to facilitate secretion. The lipase proteins are comprised of two principal domains (Winkler, K., D'Arcy, A., and Hunziker, W. (1990) Nature 343, 771-774). The amino terminal domain contains the catalytic site while the carboxyl domain is believed to be responsible for substrate binding, cofactor association, and interaction with cell receptors (Wong, H., Davis, R. C., Nikazy, J., Seebart, K. E., and Schotz, M. C. (1991) Proc. Natl. Acad. Sci. USA 88,11290-11294; van Tilbeurgh, H., Roussel, A., Lalouel, J.-M., and Cambillau, C. (1994) J. Biol. Chem. 269,4626-4633; Wong, H., Davis, R. C., Thuren, T., Goers, J. W., Nikazy, J., Waite, M., and Schotz, M. C. (1994) J. Biol. Chem. 269,10319-10323; Chappell, D. A., Inoue, I., Fry, G. L., Pladet, M. W., Bowen, S. L., Iverius, P.-H., Lalouel, J.-M., and Strickland, D. K. (1994) J. Biol. Chem. 269, 18001-18006). The overall level of amino acid homology between members of the family is 22-65%, with local regions of high homology corresponding to structural homologies which are linked to enzymatic function.

Members of the triacylglycerol lipase family share a number of conserved structural features. One such feature is the "GXSXG" motif, in which the central serine residue is one of the three residues comprising the "catalytic triad" (Winkler, K., D'Arcy, A., and Hunziker, W. (1990) Nature 343, 771-774; Faustinella, F., Smith, L. C., and Chan, L. (1992) Biochemistry 31,7219-7223). Conserved aspartate and histidine residues make up the balance of the catalytic triad. A short span of 19-23 amino acids (the "lid region") forms an amphipathic helix structure and covers the catalytic pocket of the enzyme (Winkler, K., D'Arcy, A., and Hunziker, W. (1990) Nature 343, 771-774). Comparisons between hepatic and lipoprotein lipase have demonstrated that differences in triacylglycerol lipase and phospholipase activities of the enzymes are in part mediated by this lid region (Dugi, K. A., Dichek H. L., and Santamarina-Fojo, S.

(1995) J. Biol. Chem. 270, 25396-25401). Triacylglycerol lipases possess varying degrees of heparin binding activity. Lipoprotein lipase has the highest affinity for heparin, and this binding activity has been mapped to stretches of positively charged residues in the amino terminal domain (Ma, Y., Henderson, H. E., Liu, M.-S., Zhang, H., Forsythe, I. J., Clarke-Lewis, I., Hayden, M. R., and Brunzell, J. D. J. Lipid Res. 35, 2049-2059).

The genetic sequences encoding human pancreatic lipase, hepatic lipase and lipoprotein lipase have been reported (GenBank accession #M93285, #J03540, and #M15856 respectively). The messenger RNAs of human hepatic lipase and pancreatic lipase are approximately 1.7 and 1.8 kilobases in length respectively. Two mRNA transcripts of 3.6 and 3.2 kilobases are produced from the human lipoprotein lipase gene. (Ranganathan, G., Ong, J. M., Yukht, A., Saghizadeh, M., Simsolo, R. B., Pauer, A., and Kern, P. A. (1995) J. Biol. Chem. 270, 7149-7155).

Compounds that Affect Lipase Activity

The present invention relates to the compounds of formula (I)

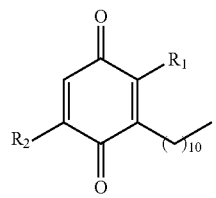

and derivatives thereof including but not limited to polymorphs, isomers and prodrugs thereof, geometric or optical isomers thereof, and pharmaceutically acceptable esters, ethers, carbamates of such compounds, all solvates and hydrates thereof and all salts thereof, wherein: $R_1$ and $R_2$ are each independently selected from the group consisting of hydrogen, $C_3$-$C_{13}$ alkyl, $C_1$-$C_{20}$ haloalkyl, $C_2$-$C_{13}$ alkenyl, $C_2$-$C_{13}$ alkynyl, $C_4$-$C_6$ cycloalkyl, $C_4$-$C_6$ cycloalkenyl, $C_1$-$C_{13}$ alkoxyalkyl, $C_1$-$C_5$ alkylcycloalkyl, $C_1$-$C_5$ alkylcycloalkenyl, $C_1$-$C_{13}$ alkylamine, $C_1$-$C_{13}$ arylamine, C(O)$C_1$-$C_6$ alkyl, O—C(O)$C_1$-$C_6$ alkyl, heterocycloalkyl, aryl, alkylaryl, C(O)aryl and O—C(O)aryl; wherein each of the foregoing groups may optionally bear 1 to 6 substituents independently selected from hydrogen, halo, nitro, amino, cyano, isocyano, thio, $C_1$-$C_6$ alkyl, cycloalkyl, aryl, alkoxy, and aryloxy groups. However in accordance with the present invention $R_1$ and $R_2$ are not methyl, methoxy, ethyl, ethoxy, phenyl, and hydroxy.

In another embodiment, the invention relates to compounds of formula (II):

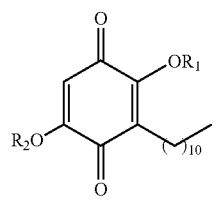

and derivatives thereof including but not limited to polymorphs, isomers and prodrugs thereof, geometric or optical isomers thereof, and pharmaceutically acceptable esters, ethers, carbamates of such compounds, all solvates and hydrates thereof and all salts thereof, wherein: $R_1$ and $R_2$ are each independently selected from the group consisting of $C_3$-$C_{13}$ alkyl, $C_1$-$C_{20}$ haloalkyl, $C_2$-$C_{13}$ alkenyl, $C_2$-$C_{13}$ alkynyl, $C_4$-$C_6$ cycloalkyl, $C_4$-$C_6$ cycloalkenyl, $C_1$-$C_{13}$ alkoxyalkyl, $C_1$-$C_5$ alkylcycloalkyl, $C_1$-$C_5$ alkylcycloalkenyl, $C_1$-$C_{13}$ alkylamine, $C_1$-$C_{13}$ arylamine, C(O)$C_1$-$C_6$ alkyl, heterocycloalkyl, aryl, alkylaryl, and C(O)aryl; wherein each of the foregoing groups may optionally bear 1 to 6 substituents independently selected from hydrogen, halo, nitro, amino, cyano, isocyano, thio, $C_1$-$C_6$ alkyl, cycloalkyl, aryl, alkoxy, and aryloxy groups. However in accordance with the present invention $R_1$ and $R_2$ are not methyl, ethyl, and phenyl.

In another embodiment, the invention relates to compounds of formula (III):

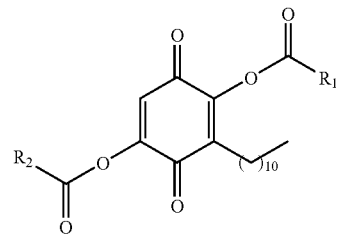

and derivatives thereof including but not limited to polymorphs, isomers and prodrugs thereof, geometric or optical isomers thereof, and pharmaceutically acceptable esters, ethers, carbamates of such compounds, all solvates and hydrates thereof and all salts thereof, wherein: $R^1$ and $R^2$ are each independently selected from the group consisting of hydrogen, $C_1$-$C_{13}$ alkyl, $C_1$-$C_{20}$ haloalkyl, $C_2$-$C_{13}$ alkenyl, $C_2$-$C_{13}$ alkynyl, $C_4$-$C_6$ cycloalkyl, $C_4$-$C_6$ cycloalkenyl, $C_1$-$C_{13}$ alkoxyalkyl, $C_1$-$C_{13}$ alkylamine, $C_1$-$C_{13}$ arylamine, $C_1$-$C_5$ alkylcycloalkyl, $C_1$-$C_5$ alkylcycloalkenyl, C(O)$C_1$-$C_6$ alkyl, heterocycloalkyl, aryl, alkylaryl, and C(O)aryl; wherein each of the foregoing groups may optionally bear 1 to 6 substituents independently selected from hydrogen, halo, nitro, amino, cyano, isocyano, thio, $C_1$-$C_6$ alkyl, cycloalkyl, aryl, alkoxy, and aryloxy groups.

In one embodiment compounds of Formula (III) have $R_1$ and $R_2$ independently selected from C(O)aryl, C(O)alkylaryl, C(O)haloaryl, C(O)nitroaryll, or C(O)alkoxyaryl.

Other embodiments relate to compounds of Formula (III), wherein $R_1$ and $R_2$ are independently selected from methyphenylcarbonyl, ethylphenylcarbonyl, propylphenylcarbonyl, butylphenylcarbonyl, chlorophenylcarbonyl, bromopheynylcabonyl, iodophenylcarbonyl, fluorophenylcarbonyl, nitrophenylcarbonyl, methoxyphenylcarbonyl, or ethoxyphenylcarbonyl.

Further embodiments relate to compounds of Formula (III), wherein $R_1$ and $R_2$ are independently selected from 2-methyphenylcarbonyl, 3-methyphenylcarbonyl, 4-methyphenylcarbonyl, 4-ter-butylphenylcarbonyl, 2-chlorophenylcarbonyl, 3-chlorophenylcarbonyl, 4-chlorophenylcarbonyl, 2-bromopheynylcabonyl, 3-bromopheynylcabonyl, 4-bromopheynylcabonyl, 2-iodophenylcarbonyl, 3-iodophenylcarbonyl, 4-iodophenylcarbonyl, 2-fluorophenylcarbonyl, 3-fluorophenylcarbonyl, 4-fluorophenylcarbonyl, 2-nitrophenylcarbonyl, 3-nitrophenylcarbonyl, 4-nitrophenylcarbonyl, 2-methoxyphenylcarbonyl, 3-methoxyphenylcarbonyl, and 4-methoxyphenylcarbonyl.

Accordingly, the present invention also encompasses prodrugs of compounds of the present invention. The term "prodrug" includes a compound that is transformed in vivo to yield a compound of Formulas (I), (II) or (III). Information about the use of prodrugs may be found in "Pro-drugs as Novel Delivery Systems," Vol. 14 of the A.C.S. Symposium Series, by T. Higuchi and W. Stella, and in Bioreversible Carriers in Drug Design, ed. Edward B. Roche, American Pharmaceutical Association and Pergamon Press, 1987.

Suitable active metabolites of compounds within the scope of Formulas (I), (II) or (III), in any suitable form, are also included herein.

The compounds of the present invention may contain asymmetric or chiral centers, and therefore may exist in different stereoisomeric forms. All suitable optical isomers and stereoisomeric forms of the compounds of the present invention as well as mixtures thereof, including racemic mixtures, form part of the present invention. In addition, the present invention embraces all geometric and positional isomers. For example, if a compound of the present invention incorporates a double bond or a fused ring, the cis- and trans-forms, as well as mixtures, are embraced within the scope of the invention. With respect to such compounds, the present invention includes the use of a racemate, a single enantiomeric form, a single diastereomeric form, or mixtures thereof, as suitable. Moreover, such compounds may also exist as tautomers. Accordingly, the present invention relates to the use of all such suitable tautomers and mixtures thereof. Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers or by resolution of the racemic form by recrystallization techniques, by synthesis from optically-active starting materials, by chiral synthesis, or by chromatographic separation using a chiral stationary phase. Also, some of the compounds of the present invention may be atropisomers (e.g., substituted biaryls) and are considered as part of this invention. Enantiomers can also be separated by use of a chiral HPLC column.

Moreover, some compounds of the present invention may exhibit polymorphism. The scope of the present invention includes all polymorphic forms of the compounds according to the invention, which forms the further aspect of the invention. It is to be understood that the present invention encompasses any and all racemic, optically-active, polymorphic and stereoisomeric forms, or mixtures thereof, which form or forms possess properties useful in the treatment of the conditions indicated herein.

Furthermore, the present invention also include isotopically-labeled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine, iodine, and chlorine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{123}I$, $^{125}I$ and $^{36}Cl$, respectively. Certain isotopically-labeled compounds of the present invention (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and delectability. Further, substitution with heavier isotopes such as deuterium (i.e., 2H) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$, and $^{18}F$ are useful for positron emission tomography (PET) studies to examine substrate receptor occupancy. Isotopically labeled compounds of the present invention can generally be prepared by procedures analogous to those disclosed in the Examples herein below, by substituting an isotopically labeled reagent for a non-isotopically labeled reagent.

It is an aspect of the invention to provide the process for preparing compounds of Formulas (I), (II) or (III). Those skilled in the art will understand from this disclosure how to prepare the most preferred compounds of the present invention using any suitable known method. Compounds of Formulas (I), (II) or (III) and, unless otherwise indicated, $R_1$, $R_2$, as described above may be conveniently prepared according to Scheme I.

In addition, the examples provided herein further illustrate the preparation of the compounds of the present invention. Moreover, those skilled in the art will understand from the present disclosure how to modify Scheme I, and the details of the examples described hereinafter to prepare any specific compound of Formulas (I), (II) or (III) of the present invention as desired. It should be understood that Scheme I is provided solely for the purposes of illustration and depicts potential route for synthesizing compounds of Formulas (I), (II) or (III) and does not limit the invention. Those skilled in the art will appreciate that other synthetic routes may be used to synthesize the compounds of the present invention. Although specific starting materials and reagents are depicted in the Scheme I illustrated below, the suitable substitution can be easily made to provide a variety of derivatives and reaction conditions. In addition, many of the compounds prepared by the method described below can be further modified in light of the disclosure using the conventional chemistry known to those skilled in the art.

Scheme I:

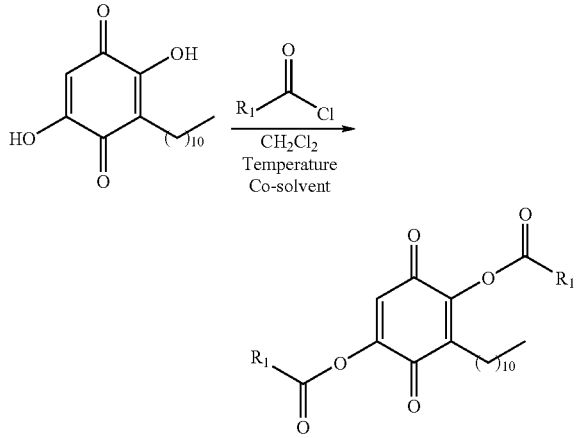

Scheme I depicts a general protocol for preparing compound of Formulas (I), (II) or (III) starting from 2,5- dihydroxy-3-undecyl-1,4-benzaquinone or its oxime, or substituted oxime, or suitable salt or analogs thereof. The starting material—2,5-dihydroxy-3-undecyl-1,4-benzoquinone—is reacted with alkyl chloride or acyl chloride, or aryl chloride or aroyl chloride, or substituted aryl chloride or substituted aroyl chloride in a suitable inert halogenated solvent (e.g. dichloromethane) in presence of a suitable aromatic base (e.g. pyridine) under the controlled condition such as at a temperature of about 10° C. to about 40° C. over a period of about 1 hour to about 24 hours to yield the compound of Formulas (I), (II) or (III) in crude form. Conventional methods and/or techniques of separation and purification known to one of ordinary skill in the art can be used to isolate & purify the compounds of the present invention. Such techniques will be well known to one of ordinary skill in the art and may include, for example, all types of chromatography (high pressure liquid chromatography (HPLC), column chromatography using common adsorbents such as silica gel, and thin-layer chromatography), recrystallization, and differential (i.e., liquid-liquid) extraction techniques.

Lipase Related Diseases and Conditions

It is an aspect of the present invention to provide compounds of Formulas (I), (II) or (III) and derivatives thereof for use as therapeutically active substances.

The compounds of the present invention as disclosed above are useful for reducing or inhibiting activity of lipase gene family enzymes for treatment, amelioration or prevention of lipase gene family enzyme mediated diseases. The compounds are useful in reducing or inhibiting metabolism, absorption, and accumulation of fat at various levels including body fluid, cellular, and tissue levels in body by inhibiting or reducing the activity of enzymes belonging to lipase gene family. Thus, the compounds of the present inventions and derivatives thereof including compositions thereof are useful in reducing or inhibiting activity of enzymes of lipase gene family participating in metabolism, absorption, and accumulation of lipids in body at various levels including body fluid, cellular and tissue level for treatment, amelioration or prevention of diseases mediated by lipase gene family enzyme including but not limited to overweight or obesity, hyperlipidemia, hypercholesterolemia, hypertriglyceridemia, pancreatitis, hyperglycemia, atherosclerosis, metabolic syndromes, other cardiovascular diseases, and other metabolic disorders.

In another aspect the compounds of the present invention and derivatives thereof including compositions thereof are useful in prevent or treat cellular and tissue damage caused by microbial pathogens secreting lipases.

In another aspect the compounds of the present invention and derivatives thereof including compositions thereof are also useful for skin, hair care or cosmetic preparation.

It is an embodiment of the present invention to provide method for treating conditions, diseases and/or disorders mediated by enzymes belonging to the lipase gene family including but not limited to overweight or obesity, hyperlipidemia, hypercholesterolemia, hypertriglyceridemia, pancreatitis, hyperglycemia, atherosclerosis, metabolic syndromes, other cardiovascular diseases, and other metabolic disorders by reducing or inhibiting metabolism, absorption, and accumulation of fat at various levels including body fluid, cellular, and tissue levels in body by inhibiting or reducing the activity of enzymes belonging to lipase gene family in mammal including a human being which comprises administering to said mammal an effective treating amount of a compound of Formulas (I), (II) or (III) or derivatives thereof.

In another embodiment the present invention provides method for treating or preventing cellular and tissue damage caused by microbial pathogens secreting lipases by inhibiting or reducing the activity of enzymes belonging to lipase gene family in mammal including a human being which comprises administering to said mammal an effective treating amount of a compound of Formulas (I), (II) or (III) or derivatives thereof.

Accordingly it is one embodiment of the present invention to provide a pharmaceutical composition comprising a therapeutically effective amount of a compound of Formulas (I), (II) or (III) or a derivative thereof and a pharmaceutically acceptable inert adjuvant, diluent or carrier. Alternatively a pharmaceutical composition may comprise of at least one additional pharmaceutically active agent. Additional active pharmaceutical agent may be selected from chemically synthesized compounds or those derived from natural origin having desired pharmacological activity.

Formulations

A compound of Formulas (I), (II) or (III) or a derivative thereof can be administered in any conventional oral, buccal, nasal, by inhalation spray in unit dosage form, parenteral, (for example, intravenous, intramuscular, subcutaneous intrasternal or by infusion techniques), topical (for example, powder, ointment or drop), transdermal, intracistemal, intravaginal, intraperitoneal, intravesical, or rectal. In another aspect of the invention, the compound of the present invention and at least one other pharmaceutically active agent may be administered either separately or in the pharmaceutical composition comprising both. It is generally preferred that such administration be oral. However, if the subject being treated is unable to swallow, or oral administration is otherwise impaired or undesirable, parenteral or transdermal administration may be appropriate.

A compound of Formulas (I), (II) or (III) or a derivative thereof can be administered in the form of any modified release, controlled release or timed release formulations. (see, e.g., Langer, Science 249:1527-1533 (1990)). In one embodiment, a pump can be used (Langer, Science 249: 1527-1533 (1990); Sefton, CRC Crit. Ref. Biomed. Eng. 14:201 (1987); Buchwald et al., Surgery 88:507 (1980); and Saudek et al., N. Engl. J. Med. 321:574 (1989)). In another embodiment, polymeric materials can be used (see Medical Applications of Controlled Release (Langer and Wise eds., 1974); Controlled Drug Bioavailability, Drug Product Design and Performance (Smolen and Ball eds., 1984); Langer and Peppas, J. Macromol. Sci. Rev. Macromol. Chem. 23:61 (1983); Levy et al., Science 228:190 (1985); During et al., Ann. Neurol. 25:351 (1989); and Howard et al., J. Neurosurg. 71:105 (1989)).

The dose of a compound of Formulas (I), (II) or (III) or derivatives thereof to be administered to a mammal including human or animal for the purposes as mentioned above is not specifically limited. Rather it is widely variable and subject to the pathologies, conditions, symptoms, or age of the subject and judgment of the attending physician or veterinarian. The general range of effective administration rates of the compounds of the present invention is from about 0.001 mg/kg body weight to about 100 mg/kg body weight of the subject per day. A preferred range of effective administration rates of the compounds of this invention is from about 0.01 mg/kg body weight to about 50 mg/kg body weight of the subject per day. Amounts are selected based on various factors, including the milieu to which the composition is administered, the site of the cells to be treated, the age, health, gender, and weight of a patient or animal to be treated, etc. Useful amounts include, 1, 5, 15, 20, 25, 30, 40, 60, 150, 200 milligrams, 1 gm, 2 gm, 3 gm, and ranges between 10 milligrams-100 grams, 50 milligrams-5 grams, 100 milligrams-10 grams, 250 milligrams-2.5 grams, 500 milligrams-1.25 grams. etc., per dosage. While it may be practical to administer the daily dose of a compound of this invention, in portions, at various hours of the day, in any given case, the amount of compound of this invention will depend on such factors as the solubility of the compound, prodrug, isomer or pharmaceutically acceptable salt of this invention, the formulation used and the route of administration (e.g., orally, transdermally, parenterally or topically).

Dosages of the compounds of the present invention can be administered to humans by any suitable route, with oral administration being preferable. Individual oral dosage form for example, tablets or capsules should generally contain from about 0.1 mg to about 100 mg of compound of this invention, in a suitable pharmaceutically acceptable vehicle, diluent or carrier. Dosages for intravenous administration are generally within the range of from about 0.1 mg to about 10 mg per single dose as required. For intranasal or inhaler administration, the dosage is generally formulated as from about a 0.1% to about a 1% (w/v) solution. In practice, the physician will determine the actual dosage, which will be most suitable for an individual patient, and it will vary with, e.g., age, weight and response of the particular patient. The above dosages are exemplary of the average case but there can, of course, be individual instances where higher or lower dosage ranges are possible, such dosages of compounds of this invention, are within the scope of the present invention.

It is another preferred embodiment of the present invention to provide compounds of Formulas (I), (II) or (III) and derivatives thereof for manufacturing pharmaceutical formulations for the prophylaxis and therapy of conditions, diseases and/or disorders mediated by enzymes belonging to the lipase gene family including but not limited to overweight or obesity, hyperlipidemia, hypercholesterolemia, hypertriglyceridemia, pancreatitis, hyperglycemia, atherosclerosis, metabolic syndromes, other cardiovascular diseases, and other metabolic disorders. The pharmaceutical formulation comprising a compound of Formulas (I), (II) or (III) or the derivatives thereof may be formulated in a conventional manner known to those skilled at the art using one or more pharmaceutically acceptable diluent, carrier, or vehicle.

For oral administration the pharmaceutical formulations that may be used in the present invention include tablets, chewable tablets, controlled release tablets, capsules, lozenges, granules, powders, pills, microcapsules, elixirs, syrups, and suspensions.

In general tablets can be prepared by methods known in pharmaceutical science by direct compression, by wet granulation, or by dry granulation. Their formulations usually incorporate diluents, binders, lubricants and disintegrators as well as a compound of this invention. Common diluents include, for example, various types of starch, lactose, mannitol, kaolin, calcium phosphate or sulfate, inorganic salts such as sodium chloride and powdered sugar. Powdered cellulose derivatives may also be used. Common tablet binders include substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant is generally necessary in a tablet formulation to prevent the tablet and punches from sticking in the die. The lubricant is chosen from such slippery solids as talc, magnesium and calcium stearate, stearic acid and hydrogenated vegetable oils. Tablet disintegrators include substances, which swell when wetted to break up the tablet and release a compound, prodrug, isomer or pharmaceutically acceptable salt of this invention. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethylcellulose, for example, may be used as well as sodium lauryl sulfate. Tablets are often coated with sugar as a flavor and sealant, or with film-forming protecting agents to modify the dissolution properties of the tablet. The compounds of the invention may also be formulated as chewable tablets, by using large amounts of pleasant-tasting substances such as mannitol in the formulation, as is now well-established in the art.

As discussed above, the effect of a compound of this invention may be controlled that is delayed or prolonged or time bound by proper formulation. For example, a slowly soluble pellet of a compound of this invention may be prepared and incorporated in a tablet or capsule. The technique may be improved by making pellets of several different dissolution rates and filling capsules with a mixture of the pellets. Tablets or capsules may be coated with a film, which resists dissolution for a predictable period of time.

Capsules can be prepared by mixing a compound of the invention with a suitable diluent and filling the proper amount of the mixture in capsules. The usual diluents include inert powdered substances such as starch of many different kinds, powdered cellulose, especially crystalline and microcrystalline cellulose, sugars such as fructose, mannitol and sucrose, grain flours and similar edible powders.

Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending/viscosity enhancing agents (e.g. sorbitol syrup, methyl cellulose or hydrogenated edible fats); emulsifying agents (e.g. lecithin or acacia); non-aqueous vehicles (e.g. almond oil, oily esters or ethyl alcohol, medium chain triglycerides); and preservatives (e.g. methyl or propyl p-hydroxybenzoates or sorbic acid).

For parenteral administration the compounds of the invention may be formulated in the form of an injection, including using conventional catheterization techniques or infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulating agents such as suspending, stabilizing and/or dispersing agents. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid and surfactants such as, for example, hydroxypropyl cellulose, also the pH of the solution being suitably adjusted and buffered, where necessary. Generally oily solutions are suitable for intra-articular, intramuscular and subcutaneous injection purposes. Such aqueous solutions are suitable for intravenous injection purposes. Alternatively, the active ingredient may be in powder form for reconstitution with a suitable vehicle, e.g. sterile pyrogen-free water, before use. The parenteral preparations may also be made long-acting by dissolving or suspending a compound, prodrug, isomer or pharmaceutically acceptable salt of this invention, as the case may be, in oily or emulsified vehicles which allow it to disperse only slowly in the serum.

For intranasal administration or administration by inhalation, the compounds of the present invention are conveniently delivered in the form of a solution or suspension from a pump spray container that is squeezed or pumped by the patient or as an aerosol spray presentation from a pressurized container or a nebulizer, with the use of a suitable propellant, e.g. dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Capsules and cartridges (made, for example, from gelatin) for use in an inhaler or insufflator may be formulated containing a powder mix of a compound of the invention and a suitable powder for inhalation base such as lactose or starch.

The compounds of this invention may also be administered topically and this may be done by way of, e.g., creams, jellies, salves, lotions, gels, pastes, ointments, and the like, in accordance with standard pharmaceutical practice. The compounds of the present invention may also be administered transdermally (e.g., through the use of a patch).

Any suitable formulation for transdermal application comprising a compound of the present invention may be employed and such formulations would generally also contain a suitable transdermal carrier, e.g., an absorbable pharmacologically acceptable solvent to promote and assist passage of the compounds through the subject's skin. For example, suitable transdermal devices may comprise the form of a bandage having a backing member and a reservoir containing the subject compound. Such bandage-type transdermal devices may further include suitable carriers, rate-controlling barriers, and means for securing the transdermal device to the subject's skin.

Where it is desired to administer a compound of this invention as a suppository, any suitable base can be used. Cocoa butter is a traditional suppository base, which may be modified by the addition of waxes to raise its melting point. Water-miscible suppository bases comprising, particularly, polyethylene glycols of various molecular weights are in wide use.

In other embodiments a compound of this invention may be incorporated in food, or beverages.

The compounds of this invention may also be administered to a mammal other than a human. The method of administration and the dosage to be administered to such a mammal will depend, for example, on the animal species and the disease or disorder being treated. The compounds of this invention may be administered to animals in any suitable manner, e.g., orally, parenterally or transdermally, in any suitable form such as, for example, a capsule, bolus, tablet, pellet, e.g., prepared by admixing a compound, prodrug, isomer or pharmaceutically acceptable salt of this invention with a suitable diluent such as carbowax or carnuba wax together with a lubricant, liquid drench or paste, e.g., prepared by dispersing a compound of this invention in a pharmaceutically acceptable oil such as peanut oil, sesame oil or corn oil. The compounds, prodrugs, isomers or pharmaceutically acceptable salts of this invention may also be administered to animals as an implant. Such formulations are prepared in a conventional manner in accordance with standard veterinary practice. As an alternative, the compounds of this invention may be administered with the water supply, e.g., in the form of a liquid or water-soluble concentrate. In addition, the compounds of this invention, e.g., within the pharmaceutical compositions of the invention, may be administered in the animal feedstuff, e.g., a concentrated feed additive or premix may be prepared for mixing with the normal animal feed, commonly along with a suitable carrier therefore. The carrier facilitates uniform distribution of the compound, prodrug, isomer or pharmaceutically acceptable salt of this invention in the, e.g., finished feed with which the premix is blended. Suitable carriers include, but are not limited to, liquids, e.g., water, oils such as soybean, corn, cottonseed, or volatile organic solvents, and solids, e.g., a small portion of the feed or various suitable meals including alfalfa, soybean, cottonseed oil, linseed oil, corncob, corn, molasses, urea and bone, and mineral mixes.

In another aspect of the present invention the biological assays carried out using compounds of Formulas (I), (II) and (III) demonstrate potent inhibition of lipases.

The following examples illustrate the embodiments of the present invention. It is to be understood, however, that the embodiments of the invention are not limited to the specific details of these Examples, as other variations thereof will be known, or apparent in light of the instant disclosure, to one of ordinary skill in the art.

EXAMPLES

Example 1

2,5-Di-O-(3-fluorophenylcarbonyl)-3-undecyl-1,4-benzoquinone

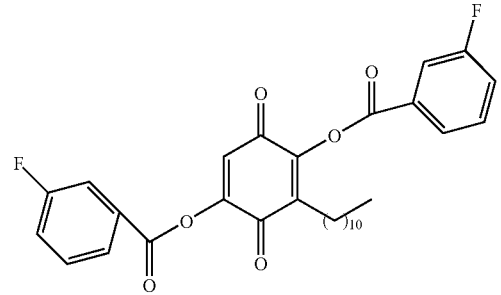

Synthesis of Structure # 2; 2,5-bis-(3-fluorophenylcarbonyloxy)-3-undecyl-1,4-benzoquinone To a stirred solution of 2,5-dihydroxy-3-undecyl-1,4-benzoquinone (1.0 gm, 3.4 mmole) in dichloromethane (20 mL) was added pyridine (1.1 mL, 13.6 mmole). To this, was added 3-fluoro benzoylchloride (1.35 gm, 8.5 mmole) at 15-20° C. and stirred, allowed to attain 30° C. and stirring was continued for 3 h (TLC). The organic layer was extracted with dichloromethane, washed (water, brine), dried ($Na_2SO_4$), concentrated to crude which was purified by $SiO_2$ column chromatography (10-20% EtOAc in hexane) to a pure mass (0.96 g, 52.7%).

$^1$H NMR (300 MHz, $CDCl_3$) δ: 0.87 (t, 3H, J=6.9 Hz), 1.0-1.6 (m, 18H), 2.5 (t, 2H, J=7.6 Hz), 6.8 (s, 1H), 7.3-8.0 (m, 8H). TOF MS ES: 539 (M+H). Mp. 73.2-75.6° C.

Example 2

2,5-Di-O-(4-tert-butylphenyl carbonyl)-3-undecyl-1,4-benzoquinone

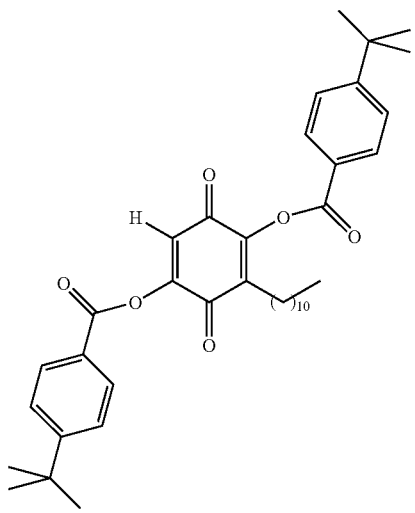

Synthesis of Structure# 3; 2,5-bis-(4-tert-butylphenylcarbonyloxy)-3-undecyl-1,4-benzoquinone To a stirred solution of 2,5-dihydroxy-3-undecyl-1,4-benzoquinone (1.0 gm, 3.4 mmole) in dichloromethane (20 mL) was added pyridine (1.1 mL, 13.6 mmole). To this, was added 4-tert-butyl benzoylchloride (1.67 gm, 8.5 mmole) at 15-20° C. and stirred, allowed to attain 30° C. and stirring was continued for 3 h (TLC). The organic layer was extracted with dichloromethane, washed (water, brine), dried ($Na_2SO_4$), concentrated to crude which was purified by $SiO_2$ column chromatography (10-20% EtOAc in hexane) to a pure mass (1.47 g, 28.3%).

$^1$H NMR (300 MHz, $CDCl_3$) δ: 0.86 (t, 3H, J=7.0 Hz), 1.0-1.6 (m, 36H), 2.5 (t, 2H, J=7.5 Hz), 6.75 (s, 1H), 7.4-8.2 (m, 8H). TOF MS ES: 615 (M+H). Viscous mass.

Example 3

2,5-Di-O-(2-fluorophenylcarbonyl)-3-undecyl-1,4-benzoquinone

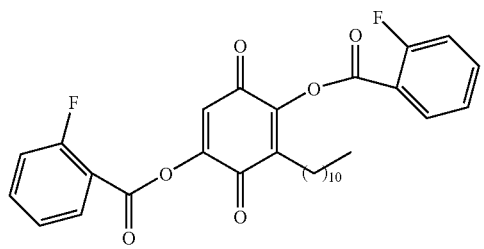

Synthesis of Structure # 4;
2,5-bis-(2-fluorophenylcarbonyl oxy)-3-undecyl-1,4-benzoquinone To a stirred solution of 2,5-dihydroxy-3-undecyl-1,4-benzoquinone (1.0 gm, 3.4 mmole) in dichloromethane (20 mL) was added pyridine (1.1 mL, 13.6 mmole). To this, was added 2-fluoro benzoylchloride (1.35 gm, 8.5 mmole) at 15-20° C. and stirred, allowed to attain 30° C. and stirring was continued for 3 h (TLC). The organic layer was extracted with dichloromethane, washed (water, brine), dried ($Na_2SO_4$), concentrated to crude which was purified by $SiO_2$ column chromatography (10-20% EtOAc in hexane) to a pure mass (0.96 g, 52.7%).

$^1$H NMR (300 MHz, $CDCl_3$) δ: 0.87 (t, 3H, J=6.9 Hz), 1.1-1.7 (m, 18H), 2.5 (t, 2H, J=8.0 Hz), 6.8 (s, 1H), 7.2-8.2 (m, 8H). TOF MS ES: 539 (M+H). Mp. 66.2-68° C.

Example 4

2,5-Di-O-(2-bromophenylcarbonyl)-3-undecyl-1,4-benzoquinone

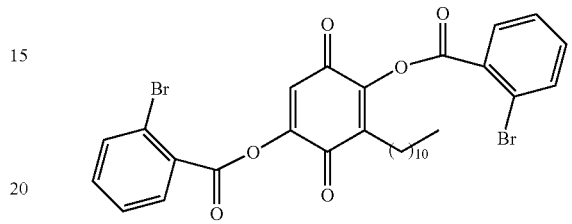

Synthesis of Structure # 5; 2,5-bis-(2-bromophenylcarbonyloxy)-3-undecyl-1,4-benzoquinone To a stirred solution of 2,5-dihydroxy-3-undecyl-1,4-benzoquinone (1.0 gm, 3.4 mmole) in dichloromethane (20 mL) was added pyridine (1.1 mL, 13.6 mmole). To this, was added 2-bromobenzoyl chloride (1.9 g, 8.5 mmole) at 15-20° C. and stirred, allowed to attain 30° C. and stirring was continued for 3 h (TLC). The organic layer was extracted with dichloromethane, washed (water, brine), dried ($Na_2SO_4$), concentrated to crude which was purified by $SiO_2$ column chromatography (10-20% EtOAc in hexane) to pure mass (1.56 g, 69.6%).

$^1$H NMR (400 MHz, $CDCl_3$) δ: 0.87 (t, 3H, J=6.8 Hz), 1.0-1.8 (m, 18H), 2.5 (t, 2H, J=6.8 Hz), 6.8 (s, 1H), 7.4-8.2 (m, 8H). TOF MS ES: 680 (25, M$^+$+Na), 682 (100, M$^+$+2+Na), 684 (25, M$^+$+4+Na). Mp. 77.1-78.6° C.

Example 5

2,5-Di-O-(3-bromophenylcarbonyl)-3-undecyl-1,4-benzoquinone

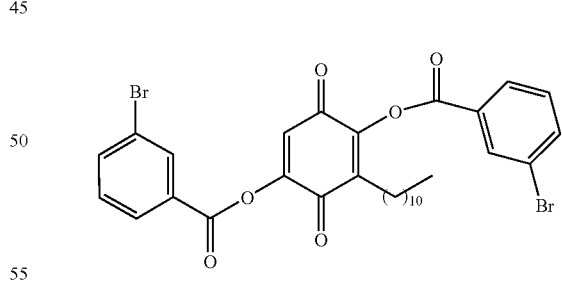

Synthesis of Structure # 6; 2,5-bis-(3-bromophenylcarbonyloxy)-3-undecyl-1,4-benzoquinone To a stirred solution of 2,5-dihydroxy-3-undecyl-1,4-benzoquinone (1.0 g, 3.4 mmole) in dichloromethane (20 mL) was added pyridine (1.1 mL, 13.6 mmole). To this, was added 3-bromobenzoyl chloride (1.9 g, 8.5 mmole) at 15-20° C. and stirred, allowed to attain 30° C. and stirring was continued for 3 h (TLC). The organic layer was extracted with dichloromethane, washed (water, brine), dried ($Na_2SO_4$), concentrated to crude which was purified by $SiO_2$ column chromatography (10-20% EtOAc in hexane) to pure mass (1.4 g, 62%).

$^1$H NMR (400 MHz, $CDCl_3$) δ: 0.87 (t, 3H, J=7.2 Hz), 1.0-1.8 (m, 18H), 2.51 (t, 2H, J=7.2 Hz), 6.8 (s, 1H), 7.4-8.4 (m, 8H). TOF MS ES: 680 (5, $M^++Na$), 682 (20, $M^++2+Na$), 684 (5, $M^++4+Na$). Mp. 98.2-99.6° C.

Example 6

2,5-Di-O-(3-chlorophenylcarbonyl)-3-undecyl-1,4-benzoquinone

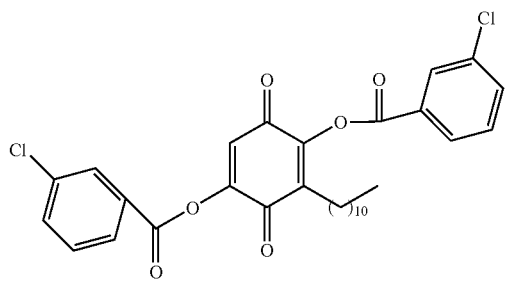

Synthesis of Structure # 7; 2,5-bis-(3-chlorophenyl-carbonyloxy)-3-undecyl-1,4-benzoquinone To a stirred solution of 2,5-dihydroxy-3-undecyl-1,4-benzoquinone (1.0 gm, 3.4 mmole) in dichloromethane (20 mL) was added pyridine (1.1 mL, 13.6 mmole). To this, was added 3-chloro benzoyl chloride (1.5 gm, 8.50 mmole) at 15-20° C. and stirred, allowed to attain 30° C. and stirring was continued for 3 h (TLC). The organic layer was extracted with dichloromethane, washed (water, brine), dried ($Na_2SO_4$), concentrated to crude which was purified by $SiO_2$ column chromatography (10-20% EtOAc in hexane) to pure mass (1.25 g, 64.4%)

$^1$H NMR (300 MHz, $CDCl_3$) δ: 0.87 (t, 3H, J=6.9 Hz), 1.1-1.7 (m, 18H), 2.5 (t, 2H, J=7.6 Hz), 6.8 (s, 1H), 7.4-8.2 (m, 8H). TOF MS ES: 593 (9, $M^++Na$), 595 (3, $M^++2+Na$). Mp. 102.8-104.6° C.

Example 7

2,5-Di-O-(2-chlorophenylcarbonyl)-3-undecyl-1,4-benzoquinone

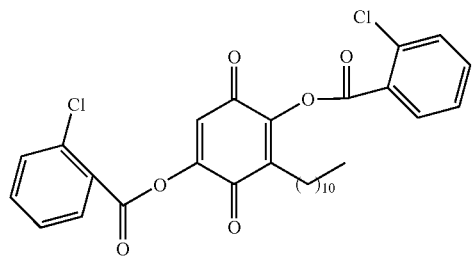

Synthesis of Structure # 8; 2,5-bis-(2-chlorophenyl-carbonyloxy)-3-undecyl-1,4-benzoquinone To a stirred solution of 2,5-dihydroxy-3-undecyl-1,4-benzoquinone (1.0 gm, 3.4 mmole) in dichloromethane (20 mL) was added pyridine (1.1 mL, 13.6 mmole). To this, was added 2-chloro benzoyl chloride (1.5 gm, 8.50 mmole) at 15-20° C. and stirred, allowed to attain 30° C. and stirring was continued for 3 h (TLC). The organic layer was extracted with dichloromethane, washed (water, brine), dried ($Na_2SO_4$), concentrated to crude which was purified by $SiO_2$ column chromatography (10-20% EtOAc in hexane) to pure mass (1.14 g, 58.7%).

$^1$H NMR (300 MHz, $CDCl_3$) δ: 0.87 (t, 3H, J=6.9 Hz), 1.0-1.6 (m, 18H), 2.5 (t, 2H, J=8.0 Hz), 6.8 (s, 1H), 7.2-8.2 (m, 8H). TOF MS ES: 593 (100, $M^++Na$), 595 (35, $M^++2+Na$). Mp. 56.2-57.8° C.

Example 8

2,5-Di-O-(4-chlorophenylcarbonyl)-3-undecyl-1,4-benzoquinone

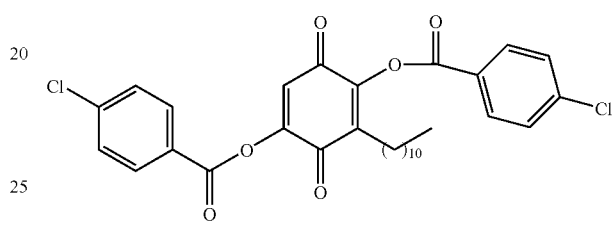

Synthesis of Structure # 9; 2,5-bis-(4-chlorophenyl-carbonyloxy)-3-undecyl-1,4-benzoquinone To a stirred solution of 2,5-dihydroxy-3-undecyl-1,4-benzoquinone (1.0 gm, 3.4 mmole) in dichloromethane (20 mL) was added pyridine (1.1 mL, 13.6 mmole). To this, was added 4-chloro benzoyl chloride (1.5 gm, 8.5 mmole) at 15-20° C. and stirred, allowed to attain 30° C. and stirring was continued for 3 h (TLC). The organic layer was extracted with dichloromethane, washed (water, brine), dried ($Na_2SO_4$), concentrated to crude which was purified by $SiO_2$ column chromatography (10-20% EtOAc in hexane) to pure mass (1.21 g, 62.4%).

$^1$H NMR (400 MHz, $CDCl_3$) δ: 0.87 (t, 3H, J=7.0 Hz), 1.1-1.7 (m, 18H), 2.5 (t, 2H, J=7.6 Hz), 6.8 (s, 1H), 7.3-8.1 (m, 8H). TOF MS ES: 593 (10, $M^++Na$), 595 (3, $M^++2+Na$). Mp. 110.2-112° C.

Example 9

2,5-Di-O-(4-bromophenylcarbonyl)-3-undecyl-1,4-benzoquinone

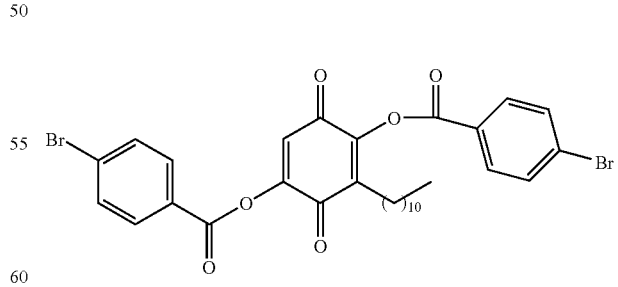

Synthesis of Structure # 10; 2,5-bis-(4-bromophe-nylcarbonyloxy)-3-undecyl-1,4-benzoquinone To a stirred solution of 2,5-dihydroxy-3-undecyl-1,4-benzoquinone (1.0 g, 3.4 mmole) in dichloromethane (20 mL) was added pyridine (1.1 mL, 13.6 mmole). To this, was added 4-bromobenzoyl chloride (1.9 g, 8.5 mmole) at 15-20° C. and stirred, allowed to attain 30° C. and stirring was continued for 3 h (TLC). The organic layer was extracted with dichloromethane, washed (water, brine), dried (Na$_2$SO$_4$), concentrated to crude which was purified by SiO$_2$ column chromatography (10-20% EtOAc in hexane) to pure mass (1.49 g, 66.5%).

$^1$H NMR (400 MHz, CDCl$_3$) δ: 0.8 (t, 3H, J=6.8 Hz), 1.0-1.8 (m, 18H), 2.5 (t, 2H, J=7.6 Hz), 6.7 (s, 1H), 7.6-8.2 (m, 8H). TOF MS ES: 680 (5, M$^+$+Na), 682 (20, M$^+$+2+Na), 684 (5, M$^+$+4+Na). Mp. 124.4-126.7° C.

Example 10

2,5-Di-O-(3-nitrophenylcarbonyl)-3-undecyl-1,4-benzoquinone

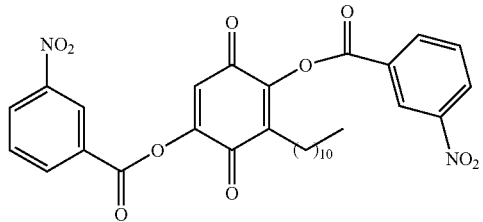

Synthesis of Structure # 11; 2,5-bis-(3-nitrophenylcarbonyloxy)-3-undecyl-1,4-benzoquinone To a stirred solution of 2,5-dihydroxy-3-undecyl-1,4-benzoquinone (1.0 gm, 3.4 mmole) in dichloromethane (20 mL) was added pyridine (1.1 mL, 13.6 mmole). To this, was added 3-nitro benzoyl chloride (1.6 gm, 8.5 mmole) at 15-20° C. and stirred, allowed to attain 30° C. and stirring was continued for 3 h (TLC). The organic layer was extracted with dichloromethane, washed (water, brine), dried (Na$_2$SO$_4$), concentrated to crude which was purified by SiO$_2$ column chromatography (10-20% EtOAc in hexane) to a pure mass (0.95 g, 47%).

$^1$H NMR (300 MHz, CDCl$_3$) δ: 0.86 (t, 3H, J=6.9 Hz), 1.1-1.6 (m, 18H), 2.5 (t, 2H, J=8.0 Hz), 6.8 (s, 1H), 7.6-8.6 (m, 8H). TOF MS ES: 593 (M+H). Mp. 112.6-114.4° C.

Example 11

2,5-Di-O-(4-methylphenylcarbonyl)-3-undecyl-1,4-benzoquinone

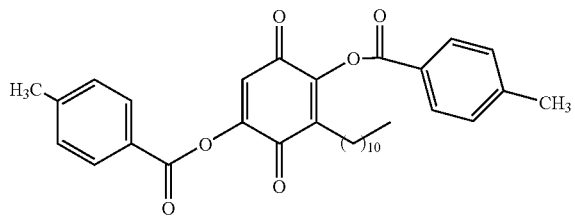

Synthesis of Structure # 12; 2,5-bis-(4-methylphenylcarbonyloxy)-3-undecyl-1,4-benzoquinone To a stirred solution of 2,5-dihydroxy-3-undecyl-1,4-benzoquinone (0.15 g, 0.5 mmole) in dichloromethane (20 mL) was added pyridine (0.41 mL, 5.1 mmole). To this, was added 4-toluoyl chloride (0.23 g, 1.53 mmole) at 15-20° C. and stirred, allowed to attain 30° C. and stirring was continued for 3.5 h (TLC). The organic layer was extracted with dichloromethane, washed (water, brine), dried (Na$_2$SO$_4$), concentrated to crude which was purified by SiO$_2$ column chromatography (10-20% EtOAc in hexanes) to pure mass (84 mg, 32%).

$^1$H NMR (300 MHz, CDCl$_3$) δ: 0.85 (m, 3H), 1.0-1.8 (m, 18H), 2.44 (m, 8H), 6.74 (s, 1H), 7.25-8.25 (m, 8H). TOF MS ES: 553 (100, M$^+$+Na). Mp. 94.8-96. 2° C.

Example 12

2,5-Di-O-(3-methylphenylcarbonyl)-3-undecyl-1,4-benzoquinone

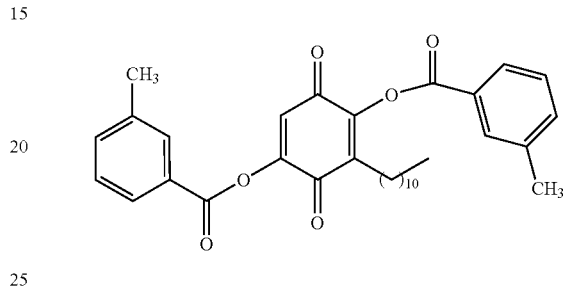

Synthesis of Structure # 13; 2,5-bis-(3-methylphenylcarbonyloxy)-3-undecyl-1,4-benzoquinone To a stirred solution of 2,5-dihydroxy-3-undecyl-1,4-benzoquinone (0.5 g, 1.7 mmole) in dichloromethane (20 mL) was added pyridine (0.55 mL, 6.8 mmole). To this, was added 3-toluoyl chloride (0.654 gm, 4.25 mmole) at 15-20° C. and stirred, allowed to attain 30° C. and stirring was continued for 3 h (TLC). The organic layer was extracted with dichloromethane, washed (water, brine), dried (Na$_2$SO$_4$), concentrated to crude which was purified by SiO$_2$ column chromatography (10-20% EtOAc in hexane) to pure mass (0.64 g, 71%).

$^1$H NMR (300 MHz, CDCl$_3$) δ: 0.85 (t, 3H, J=7.5 Hz), 1.0-1.5 (m, 18H), 2.3-2.5 (m, 8H), 6.75 (s, 1H), 7.30-7.61 (m, 5H), 7.9-8.10 (m, 3H). TOF MS ES: 553 (100, M$^+$+Na). Mp. 80.4-81.7° C.

Example 13

2,5-Di-O-(2-nitrophenylcarbonyl)-3-undecyl-1,4-benzoquinone

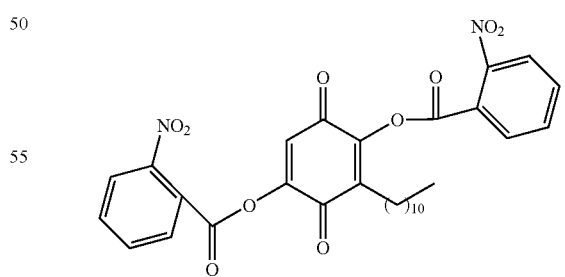

Synthesis of Structure # 14; 2,5-bis-(2-nitrophenylcarbonyloxy)-3-undecyl-1,4-benzoquinone To a stirred solution of 2,5-dihydroxy-3-undecyl-1,4-benzoquinone (1.0 gm, 3.4 mmole) in dichloromethane (20 mL) was added pyridine (1.1 mL, 13.6 mmole). To this, was added 2-nitro benzoyl chloride (1.6 gm, 8.5 mmole) at 15-20° C. and stirred, allowed to attain 30° C. and stirring was continued for 3 h (TLC). The organic layer was extracted with dichloromethane, washed (water, brine), dried (Na$_2$SO$_4$), concentrated to crude which was purified by SiO$_2$ column chromatography (10-20% EtOAc in hexane) to a pure mass (0.95 g, 47%).

$^1$H NMR (400 MHz, CDCl$_3$) δ: 0.86 (t, 3H, J=6.5 Hz), 1.1-1.6 (m, 18H), 2.6 (t, 2H, J=8.0 Hz), 6.9 (s, 1H), 7.7-8.1 (m, 8H). TOF MS ES: 615 (100, M$^+$+Na). Mp. 72.2-73.8° C.

Example 14

2,5-Di-O-(phenylcarbonyl)-3-undecyl-1,4-benzoquinone

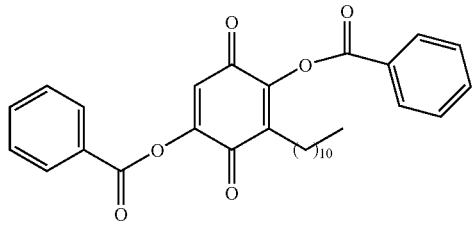

Synthesis of Structure # 15; 2,5-bis-(phenylcarbonyloxy)-3-undecyl-1,4-benzoquinone To a stirred solution of 2,5-dihydroxy-3-undecyl-1,4-benzoquinone (0.3 g, 1.02 mmole) in dichloromethane (20 mL) was added pyridine (0.3 mL, 4.08 mmole). To this, was added benzoyl chloride (0.26 gm, 2.55 mmole) at 15-20° C. and stirred, allowed to attain 30° C. and stirring was continued for 3 h (TLC). The organic layer was extracted with dichloromethane, washed (water, brine), dried (Na$_2$SO$_4$), concentrated to crude which was purified by SiO$_2$ column chromatography (10-20% EtOAc in hexanes) to pure mass (0.285 g, 56.8%).

$^1$H NMR (400 MHz, CDCl$_3$) δ: 0.85 (m, 3H), 1.10-1.68 (m, 18H), 2.50 (m, 2H), 6.77 (s, 1H), 7.42-7.64 (m, 6H), 8.11-8.22 (m, 4H). TOF MS ES: 525 (100, M$^+$+Na). Mp. 98.2-99.6° C.

Example 15

2,5-Di-O-(4-fluorophenylcarbonyl)-3-undecyl-1,4-benzoquinone

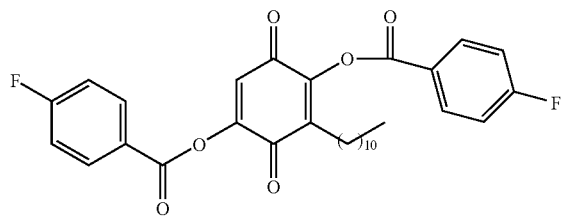

Synthesis of Structure # 16; 2,5-bis-(4-fluorophenylcarbonyloxy)-3-undecyl-1,4-benzoquinone To a stirred solution of 2,5-dihydroxy-3-undecyl-1,4-benzoquinone (1.0 gm, 3.4 mmole) in dichloromethane (20 mL) was added pyridine (1.1 mL, 13.6 mmole). To this, was added 4-fluoro benzoylchloride (1.35 gm, 8.5 mmole) at 15-20° C. and stirred, allowed to attain 30° C. and stirring was continued for 3 h (TLC). The organic layer was extracted with dichloromethane, washed (water, brine), dried (Na$_2$SO$_4$), concentrated to crude which was purified by SiO$_2$ column chromatography (10-20% EtOAc in hexane) to a pure mass (0.85 g, 46.4%).

$^1$H NMR (400 MHz, CDCl$_3$) δ: 0.86 (t, 3H, J=6.7 Hz), 1.0-1.7 (m, 18H), 2.5 (t, 2H, J=7.3 Hz), 6.7 (s, 1H), 7.1-7.2 (m, 4H), 8.1-8.2 (m, 4H). Mp. 95.8-97.7° C.

Example 16

2,5-Di-O-(3-methoxyphenylcarbonyl)-3-undecyl-1,4-benzoquinone

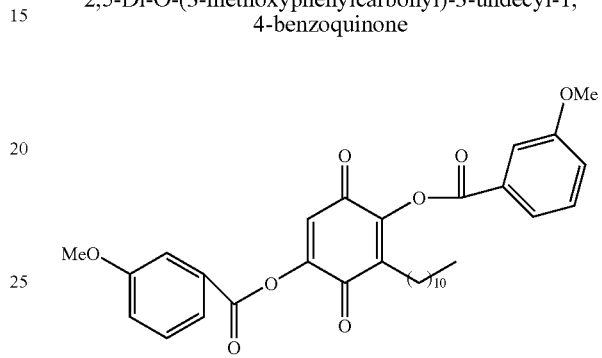

Synthesis of Structure # 17; 2,5-bis-(3-methoxyphenylcarbonyloxy)-3-undecyl-1,4-benzoquinone To a stirred solution of 2,5-dihydroxy-3-undecyl-1,4-benzoquinone (1.0 g, 3.4 mmole) in dichloromethane (20 mL) was added pyridine (1.1 mL, 13.6 mmole). To this, was added 3-methoxybenzoyl chloride (1.45 g, 8.5 mmole) at 15-20° C. and stirred, allowed to attain 30° C. and stirring was continued for 3 h (TLC). The organic layer was extracted with dichloromethane, washed (water, brine), dried (Na$_2$SO$_4$), concentrated to crude which was purified by SiO$_2$ column chromatography (10-20% EtOAc in hexane) to pure mass (1.32 g, 69%).

$^1$H NMR (400 MHz, CDCl$_3$) δ: 0.87 (t, 3H, J=7.0 Hz), 1.1-1.7 (m, 18H), 2.5 (t, 2H, J=7.9 Hz), 3.9 (s, 6H), 6.8 (s, 1H), 7.2-7.7 (m, 8H). TOF MS ES: 585 (100, M$^+$+Na). Mp. 77.1-78.6° C.

Example 17

2,5-Di-O-(4-methoxyphenylcarbonyl)-3-undecyl-1,4-benzoquinone

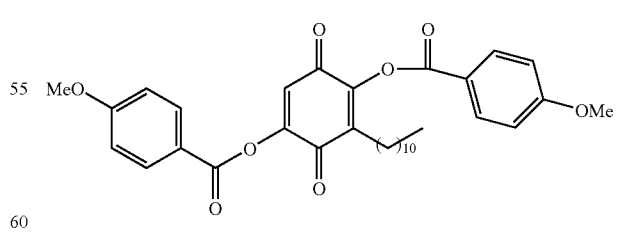

Synthesis of Structure # 18; 2,5-bis-(4-methoxyphenylcarbonyloxy)-3-undecyl-1,4-benzoquinone To a stirred solution of 2,5-dihydroxy-3-undecyl-1,4-benzoquinone (1.0 g, 3.4 mmole) in dichloromethane (20 mL) was added pyridine (1.1 mL, 13.6 mmole). To this, was added 4-methoxybenzoyl chloride (1.45 gm, 8.5 mmole) at 15-20° C. and stirred, allowed to attain 30° C. and stirring was continued for 3 h (TLC). The organic layer was extracted with dichloromethane, washed (water, brine), dried (Na$_2$SO$_4$), concentrated to crude which was purified by SiO$_2$ column chromatography (10-20% EtOAc in hexane) to pure mass (1.37 g, 71.7%).

$^1$H NMR (400 MHz, CDCl$_3$) δ: 0.87 (t, 3H, J=6.7 Hz), 1.1-1.7 (m, 18H), 2.5 (t, 2H, J=7.6 Hz), 3.9 (s, 6H), 6.9 (s, 1H), 7.0-7.2 (m, 4H), 8.10-8.13 (m, 4H). TOF MS ES: 585 (100, M$^+$+Na). Mp. 99.2-100.5° C.

Example 18

2,5-Di-O-(2-iodophenylcarbonyl)-3-undecyl-1,4-benzoquinone

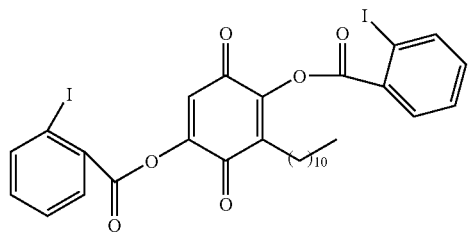

Synthesis of Structure # 19; 2,5-bis-(2-iodophenylcarbonyloxy)-3-undecyl-1,4-benzoquinone To a stirred solution of 2,5-dihydroxy-3-undecyl-1,4-benzoquinone (1.0 gm, 3.4 mmole) in dichloromethane (20 mL) was added pyridine (1.1 mL, 13.6 mmole). To this, was added 2-iodo benzoylchloride (2.26 gm, 8.5 mmole) at 15-20° C. and stirred, allowed to attain 30° C. and stirring was continued for 3 h (TLC). The organic layer was extracted with dichloromethane, washed (water, brine), dried (Na$_2$SO$_4$), concentrated to crude which was purified by SiO$_2$ column chromatography (10-20% EtOAc in hexane) to a pure mass (0.89 g, 35%).

$^1$H NMR (300 MHz, CDCl$_3$) δ: 0.87 (t, 3H, J=6.9 Hz), 1.2-1.7 (m, 18H), 2.5 (t, 2H, J=7.6 Hz), 6.8 (s, 1H), 7.2-8.2 (m, 8H). TOF MS ES: 777 (100, M$^+$+Na). Mp. 64.2-67.6° C.

Example 19

2,5-Dihydroxy-3-undecyl-p-benzoquinone

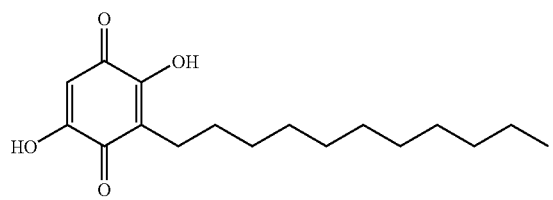

Structure # 20;
2,5-Dihydroxy-3-undecyl-p-benzoquinone (embelin)

This compound was isolated as described in Example 24.

$^1$H NMR (300 MHz, CDCl$_3$) δ: 0.87 (m, 3H), 1.0-1.75 (m, 18H), 2.43 (m, 2H), 5.99 (s, 1H), 7.66 (bs, 2H). TOF MS ES: 295 (M+H). Mp. 142-143° C.

Example 20

Assay for Lipase Inhibitory Activity

Preparation of test samples: Structures #2-#19 were dissolved in 1 mL DMSO to obtain a 10 mM stock solution, and were vortexed to dissolution and stored at 4° C. The various concentration of working samples were prepared in 0.2 M phosphate buffer, pH-8.0. This sample was used as test sample for all further assays.

Lipase assay: Lipase assay was performed by method described by Winkler and Stuckmann, 1979, with modification. (Winkler, U. K. & Stuckmann, M. Glycogen, hyaluronate, and some other polysaccharides greatly enhance the formation of exolipase by *Serratia marcescens*. J. Bacteriol. 138: 663-670 (1979)) Assay was designed, using a 96-well format. The substrate used in this assay was p-nitro phenol palmitate (Sigma, Cat No-N-2752). 4.5 mg of p-nitro phenol palmitate was dissolved in 200 µl of N,N-dimethyl formamide (Sigma, Cat No, D-4551) and volume made up to 10 ml with 0.1 M pH 8.0 phosphate buffer. Pancreatic Lipase (Sigma, Cat No. L-3126) sample was prepared by dissolving the enzyme in 0.1M phosphate buffer at a concentration of 5 mg/ml. The reaction mixture consisted of 150 µl substrate solution; 40 µl phosphate buffer (pH 8.0, 0.2 M) and 10 µl lipase solution. The reaction mixture was incubated at 37° C. and optical density was measured at 405 nm after incubation. Enzyme activity was presented in the form of international unit (IU).

Lipase activity: One enzyme unit of lipase is defined as that quantity releasing 1 nm of free phenol from the substrate (p-nitro phenol palmitate) per min per ml under the standard assay condition (Winkler and Stuckmann, 1979; Yadav R P, Saxena R K, Gupta R. Davidson W S., *Purification and characterization of a region-specific lipase from Aspergillus terreus*. Biotechnol. Appl. Biochem. (1998) 28, (243-249)). It is derived from standard graph of p-nitro phenol (Sigma, 104-8).

Lipase inhibition assay: Enzyme inhibition assay was performed in a dose dependent manner. The concentration of the synthetic analogs checked were 100 µM & 200 µM. The assay was similar to assay described above except 40 µl of test sample was used instead of phosphate buffer in control. Optical density was measured at 0 hr and following incubation at 37° C.

Enzyme Inhibition: Enzyme inhibition was presented in the term of relative activity and percentage inhibition simply on the basis of change in international unit (IU).

TABLE 1

Effect of compounds of structures #2-#20 on pancreatic lipase inhibition.

| Sample | % Inhibition (200 µM) | % Inhibition (100 µM) |
| --- | --- | --- |
| Control (no Inhibitor) | 0.00 | 0.00 |
| Structure #2 | 97.91 | 99.16 |
| Structure #3 | 99.16 | 99.54 |
| Structure #4 | 99.96 | 99.62 |
| Structure #5 | 100.00 | 100.00 |
| Structure #6 | 100.00 | 100.00 |
| Structure #7 | 100.00 | 100.00 |
| Structure #8 | 100.00 | 100.00 |
| Structure #9 | 100.00 | 98.40 |
| Structure #10 | 97.02 | 87.49 |
| Structure #11 | 97.95 | 97.38 |
| Structure #12 | 99.12 | 88.49 |
| Structure #13 | 100.00 | 100.00 |

TABLE 1-continued

Effect of compounds of structures #2-#20 on pancreatic lipase inhibition.

| Sample | % Inhibition (200 μM) | % Inhibition (100 μM) |
|---|---|---|
| Structure #14 | 61.31 | 65.88 |
| Structure #15 | 100.00 | 100.00 |
| Structure #16 | 100.00 | 89.55 |
| Structure #17 | 96.46 | 78.31 |
| Structure #18 | 94.08 | 55.64 |
| Structure #19 | 100.00 | 29.18 |
| Structure #20 | 69.46 | 67.87 |

Example 21

Determination of $IC_{50}$

Preparation of test samples: Synthetic analogues were dissolved in 1 ml DMSO to obtain a 10 mM stock solution. The samples were vortexed to dissolution and stored at 4° C. The various concentration of working samples were prepared in O.2 M phosphate buffer, pH-8.0. This sample was used as test sample for all further assays.

Lipase inhibition assay: Enzyme inhibition assay was performed in a dose dependent manner. The concentration of the synthetic analogs checked were 6.25 μM-200 μM. The assay was similar to assay described above except 40 μl of test sample was used instead of phosphate buffer in control. Optical density was measured at 0 hr and following incubation at 37° C. The enzyme activity was measured in terms of international unit (IU).

Lipase activity: One enzyme unit of lipase is defined as that quantity releasing 1 nm of free phenol from the substrate (p-nitro phenol palmitate)/min per ml under standard assay conditions. It is derived from standard graph of p-nitro phenol (Sigma, 104-8)

Percent Inhibition: Enzyme inhibition was presented in the term of % inhibition simply on the basis of change in international unit (IU).

$IC_{50}$ calculation: $IC_{50}$ of each analogue was calculated manually from dose dependent graph (6.25 μM-200 μM) of each analogue at the concentration, where the % inhibition of lipase was measured as 50% in two near straight points (above & below 50% inhibition). The value of $IC_{50}$ was derived from linear regression. The value derived is based on interpolated data.

TABLE 2

$IC_{50}$ of Structure #2-Structure #19 for pancreatic lipase inhibition.

| | $IC_{50}$ (μM) |
|---|---|
| Control (no Inhibitor) | 0.00 |
| Structure #2 | <6.25 |
| Structure #3 | <6.25 |
| Structure #4 | 7.78 |
| Structure #5 | 10.98 |
| Structure #6 | 13.51 |
| Structure #7 | 16.72 |
| Structure #8 | 20.61 |
| Structure #9 | 22.80 |
| Structure #10 | 23.69 |
| Structure #11 | 26.97 |
| Structure #12 | 41.34 |
| Structure #13 | 44.68 |

TABLE 2-continued $IC_{50}$ of Structure #2-Structure #19 for pancreatic lipase inhibition.

| | $IC_{50}$ (μM) |
|---|---|
| Structure #14 | 45.32 |
| Structure #15 | 55.57 |
| Structure #16 | 72.81 |
| Structure #17 | 81.91 |
| Structure #18 | 94.22 |
| Structure #19 | 129.39 |

Example 22

Inhibition of Lipid Absorption

Overnight fasting 4-week-old male Wistar rats (weight range: 150-200 grams) were used for the lipid absorption study. The rats were divided into two groups of 6 rats each and 100 μl of blood was drawn from orbital sinus for estimation of plasma lipid profile at 0 hour. 1 ml of fat rich liquid diet was administered PO (par orally) by gavages. Additionally, experimental group was given orally 100 μg of test compound (2,5-di-O-aroyl-3-undecyl-1,4-benzoquinone derivative Structures #2-#20) dissolved in 500 PI of vehicle; control group received same volume of vehicle.

100 μl of blood was drawn at 1 hour post-feeding for estimation of total triglycerides. Results are shown in following table. Experimental group had significantly lower level of triglycerides.

TABLE 3

Triglyceride levels

| GROUP | HOUR <0> | | HOUR <1> | |
|---|---|---|---|---|
| GROUP - 1 (control) | | | | |
| 1 | 77 | 79.5 | 127 | 135.1 |
| 2 | 72 | | 160 | |
| 3 | 54 | | 171 | |
| 4 | 66 | | 63 | |
| 5 | 79 | | 90 | |
| 6 | 129 | | 200 | |
| GROUP - 2 (experimental: Structures #2-#19) | | | | |
| 7 | 64 | 70.6 | 74 | 66.5 |
| 8 | 42 | | 48 | |
| 9 | 66 | | 91 | |
| 10 | 106 | | 67 | |
| 11 | 76 | | 50 | |
| 12 | 70 | | 69 | |

Example 23

Inhibition of Cellular Uptake of Lipids

Mouse macrophage cell line (J774A.1) were plated in 6-well culture plates ($1 \times 10^5$ cells per well) in Dulbecco's Minimum Essential Medium (DMEM) containing 10% Fetal bovine serum. 100 μg of oxidized low density lipoproteins (LDL) was added to each well. In each plate one of the compounds (Structure #2-#20) (10 μM) was added to wells in triplicate, while 3 wells were maintained as control.

Experiment was terminated after 48 hours. Cells were stained with oil Red and counterstained with hematoxylin and observed under microscope. As compared to control, treatment with Structure #2-#19 significantly inhibited uptake of LDL by macrophages.

Example 24

Extraction and Isolation of the Starting Material: 2,5-dihydroxy-3-undecyl-1,4-benzoquinone Powdered berries of *Embelia ribes* were extracted successively with petroleum ether, chloroform, ethyl acetate, methanol and water. The chloroform extract was subjected to repeated crystallization using petroleum ether as the crystallizing solvent. The crystallization step was repeated to increase the yield. The mother liquor was fractionated by silica gel column chromatography (100-200 mesh) using petroleum ether-chloroform as the eluting solvents (gradient elution) to further improve the yield. All fractions were monitored on Silica gel TLC plates (Silica gel 60 $F_{254}$, Merck) with n-propanol:n-Butanol:liquor ammonia (6:1:3) as the TLC solvent system. On the basis of TLC, similar fractions were pooled together & concentrated under reduced pressure. The compound was purified by repeated crystallization in petroleum ether to yield 140 g (3.5%) of extract. About 50 g of extract was refluxed in petroleum ether (500 ml) until the extract dissolved in the solvent. The solution was cooled to room temperature and filtered. The above procedure was repeated until compound of desired purity was obtained. The resultant compound showed The resultant compound possessed values of $^1$H NMR (300 MHz, CDCl$_3$), δ: 0.87 (m, 3H), 1.0-1.75 (m, 18H), 2.43 (m, 2H), 5.99 (s, 1H), 7.66 (bs, 2H)

All publications and patent applications cited in this specification are herein incorporated by reference as if each individual publication or patent application were specifically and individually indicated to be incorporated by reference.

Although the foregoing invention has been described in some detail by way of ion and example for purposes of clarity of understanding, it will be readily to those of ordinary skill in the art in light of the teachings of this invention that hanges and modifications may be made thereto without departing from the spirit of the appended claims.

What is claimed is:

1. A compound having formula (III),

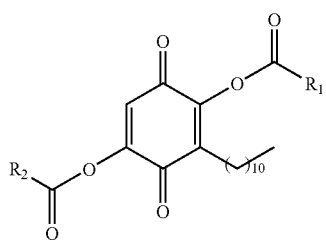

wherein R$_1$ and R$_2$ are each independently selected from the group consisting of aryl, and alkylaryl; wherein each of the foregoing groups may optionally bear 1 to 6 substituents independently selected from hydrogen, halo, nitro, amino, cyano, isocyano, thio, C$_1$-C$_6$ alkyl, cycloalkyl, aryl, alkoxy, and aryloxy groups;

a prodrug thereof, and pharmaceutically acceptable esters, ethers, carbamates, oximes of said compound, said prodrug all solvates and hydrates thereof and all salts thereof.

2. A compound selected from the group consisting of:
2,5-bis-(3-fluorophenylcarbonyloxy)-3-undecyl-1,4-benzoquinone;
2,5-bis-(4-tertiarybutylphenylcarbonyloxy)-3-undecyl-1,4-benzoquinone;
2,5-bis-(2-fluorophenylcarbonyloxy)-3-undecyl-1,4-benzoquinone;
2,5-bis-(2-bromophenylcarbonyloxy)-3-undecyl-1,4-benzoquinone;
2,5-bis-(3-bromophenylcarbonyloxy)-3-undecyl-1,4-benzoquinone;
2,5-bis-(3-chlorophenylcarbonyloxy)-3-undecyl-1,4-benzoquinone;
2,5-bis-(2-chlorophenylcarbonyloxy)-3-undecyl-1,4-benzoquinone;
2,5-bis-(4-chlorophenylcarbonyloxy)-3-undecyl-1,4-benzoquinone;
2,5-bis-(4-bromophenylcarbonyloxy)-3-undecyl-1,4-benzoquinone;
2,5-bis-(3-nitrophenylcarbonyloxy)-3-undecyl-1,4-benzoquinone;
2,5-bis-(4-methylphenylcarbonyloxy)-3-undecyl-1,4-benzoquinone;
2,5-bis-(3-methylphenylcarbonyloxy)-3-undecyl-1,4-benzoquinone;
2,5-bis-(2-nitrophenylcarbonyloxy)-3-undecyl-1,4-benzoquinone;
2,5-bis-(phenylcarbonyloxy)-3-undecyl-1,4-benzoquinone;
2,5-bis-(4-fluorophenylcarbonyloxy)-3-undecyl-1,4-benzoquinone;
2,5-bis-(3-methoxyphenylcarbonyloxy)-3-undecyl-1,4-benzoquinone;
2,5-bis-(4-methoxyphenylcarbonyloxy)-3-undecyl-1,4-benzoquinone;
2,5-bis-(2-iodophenylcarbonyloxy)-3-undecyl-1,4-benzoquinone;
a prodrug thereof, geometric or optical isomers thereof, a polymorph thereof, all solvates and hydrates thereof and all salts thereof.

3. A pharmaceutical composition comprising a compound of formula (III), according to claim 1, a prodrug thereof, pharmaceutically acceptable esters, ethers, carbamates, oximes of said compound, said prodrugs, and solvates hydrates and salts thereof;
and a pharmaceutically acceptable inert adjuvant, diluent or carrier.

4. A pharmaceutical composition comprising a compound selected from the group consisting of:
2,5-bis-(3-fluorophenylcarbonyloxy)-3-undecyl-1,4-benzoquinone;
2,5-bis-(4-tertiarybutylphenylcarbonyloxy)-3-undecyl-1,4-benzoquinone;
2,5-bis-(2-fluorophenylcarbonyloxy)-3-undecyl-1,4-benzoquinone;
2,5-bis-(2-bromophenylcarbonyloxy)-3-undecyl-1,4-benzoquinone;
2,5-bis-(3-bromophenylcarbonyloxy)-3-undecyl-1,4-benzoquinone;
2,5-bis-(3-chlorophenylcarbonyloxy)-3-undecyl-1,4-benzoquinone;
2,5-bis-(2-chlorophenylcarbonyloxy)-3-undecyl-1,4-benzoquinone;
2,5-bis-(4-chlorophenylcarbonyloxy)-3-undecyl-1,4-benzoquinone;
2,5-bis-(4-bromophenylcarbonyloxy)-3-undecyl-1,4-benzoquinone;

2,5-bis-(3-nitrophenylcarbonyloxy)-3-undecyl-1,4-benzoquinone;
2,5-bis-(4-methylphenylcarbonyloxy)-3-undecyl-1,4-benzoquinone;
2,5-bis-(3-methylphenylcarbonyloxy)-3-undecyl-1,4-benzoquinone;
2,5-bis-(2-nitrophenylcarbonyloxy)-3-undecyl-1,4-benzoquinone;
2,5-bis-(phenylcarbonyloxy)-3-undecyl-1,4-benzoquinone;
2,5-bis-(4-fluorophenylcarbonyloxy)-3-undecyl-1,4-benzoquinone;
2,5-bis-(3-methoxyphenylcarbonyloxy)-3-undecyl-1,4-benzoquinone;
2,5-bis-(4-methoxyphenylcarbonyloxy)-3-undecyl-1,4-benzoquinone; and
2,5-bis-(2-iodophenylcarbonyloxy)-3-undecyl-1,4-benzoquinone, a prodrug thereof, geometric or optical isomers thereof, a polymorph thereof, pharmaceutically acceptable esters, ethers, carbamates, oximes of said compound, said prodrugs, said isomers or said polymorphs, and solvates hydrates and salts thereof;
and a pharmaceutically acceptable inert adjuvant, diluent or carrier.

5. A pharmaceutical comprising a compound selected from the group consisting of:
2,5-bis-(3-fluorophenylcarbonyloxy)-3-undecyl-1,4-benzoquinone;
2,5-bis-(4-tertiarybutylphenylcarbonyloxy)-3-undecyl-1,4-benzoquinone;
2,5-bis-(2-fluorophenylcarbonyloxy)-3-undecyl-1,4-benzoquinone;
2,5-bis-(2-bromophenylcarbonyloxy)-3-undecyl-1,4-benzoquinone;
2,5-bis-(3-bromophenylcarbonyloxy)-3-undecyl-1,4-benzoquinone;
2,5-bis-(3-chlorophenylcarbonyloxy)-3-undecyl-1,4-benzoquinone;
2,5-bis-(2-chlorophenylcarbonyloxy)-3-undecyl-1,4-benzoquinone;
2,5-bis-(4-chlorophenylcarbonyloxy)-3-undecyl-1,4-benzoquinone;
2,5-bis-(4-bromophenylcarbonyloxy)-3-undecyl-1,4-benzoquinone;
2,5-bis-(3-nitrophenylcarbonyloxy)-3-undecyl-1,4-benzoquinone;
2,5-bis-(4-methylphenylcarbonyloxy)-3-undecyl-1,4-benzoquinone;
2,5-bis-(3-methylphenylcarbonyloxy)-3-undecyl-1,4-benzoquinone;
2,5-bis-(2-nitrophenylcarbonyloxy)-3-undecyl-1,4-benzoquinone;
2,5-bis-(phenylcarbonyloxy)-3-undecyl-1,4-benzoquinone;
2,5-bis-(4-fluorophenylcarbonyloxy)-3-undecyl-1,4-benzoquinone;
2,5-bis-(3-methoxyphenylcarbonyloxy)-3-undecyl-1,4-benzoquinone;
2,5-bis-(4-methoxyphenylcarbonyloxy)-3-undecyl-1,4-benzoquinone; and
2,5-bis-(2-iodophenylcarbonyloxy)-3-undecyl-1,4-benzoquinone, a prodrug thereof, geometric or optical isomers thereof, a polymorph thereof, pharmaceutically acceptable esters, ethers, carbamates, oximes of said compound, said prodrugs, said isomers or said polymorphs, and solvates hydrates and salts thereof;
and at least one additional pharmaceutically active agent.

6. A composition for skin or hair care or cosmetic preparation comprising a compound comprising a compound selected from the group consisting of:
2,5-bis-(3-fluorophenylcarbonyloxy)-3-undecyl-1,4-benzoquinone;
2,5-bis-(4-tertiarybutylphenylcarbonyloxy)-3-undecyl-1,4-benzoquinone;
2,5-bis-(2-fluorophenylcarbonyloxy)-3-undecyl-1,4-benzoquinone;
2,5-bis-(2-bromophenylcarbonyloxy)-3-undecyl-1,4-benzoquinone;
2,5-bis-(3-bromophenylcarbonyloxy)-3-undecyl-1,4-benzoquinone;
2,5-bis-(3-chlorophenylcarbonyloxy)-3-undecyl-1,4-benzoquinone;
2,5-bis-(2-chlorophenylcarbonyloxy)-3-undecyl-1,4-benzoquinone;
2,5-bis-(4-chlorophenylcarbonyloxy)-3-undecyl-1,4-benzoquinone;
2,5-bis-(4-bromophenylcarbonyloxy)-3-undecyl-1,4-benzoquinone;
2,5-bis-(3-nitrophenylcarbonyloxy)-3-undecyl-1,4-benzoquinone;
2,5-bis-(4-methylphenylcarbonyloxy)-3-undecyl-1,4-benzoquinone;
2,5-bis-(3-methylphenylcarbonyloxy)-3-undecyl-1,4-benzoquinone;
2,5-bis-(2-nitrophenylcarbonyloxy)-3-undecyl-1,4-benzoquinone;
2,5-bis-(phenylcarbonyloxy)-3-undecyl-1,4-benzoquinone;
2,5-bis-(4-fluorophenylcarbonyloxy)-3-undecyl-1,4-benzoquinone;
2,5-bis-(3-methoxyphenylcarbonyloxy)-3-undecyl-1,4-benzoquinone;
2,5-bis-(4-methoxyphenylcarbonyloxy)-3-undecyl-1,4-benzoquinone; and
2,5-bis-(2-iodophenylcarbonyloxy)-3-undecyl-1,4-benzoquinone, a prodrug thereof, geometric or optical isomers thereof, a polymorph thereof, pharmaceutically acceptable esters, ethers, carbamates, oximes of said compound, said prodrugs, said isomers or said polymorphs, and solvates hydrates and salts thereof;
and an inert adjuvant, diluent or carrier.

7. A method for treatment of a disease selected from the group consisting of overweight or obesity, hyperlipidemia, hypercholesterolemia, hypertriglyceridemia, and atherosclerosis comprising:
administering to the mammal a therapeutically effective amount of a compound of formula (III), according to claim 1, sufficient for inhibiting or reducing activity of lipase.

8. The method of claim 7 wherein the disease is selected from group comprising overweight or obesity, hyperlipidemia, hypercholesterolemia, hypertriglyceridemia, pancreatitis, hyperglycemia, atherosclerosis, metabolic syndromes, cardiovascular diseases, and metabolic disorders.

9. A method for treatment of a disease comprising:
administering to the mammal a compound selected from the group consisting of:
2,5-bis-(3-fluorophenylcarbonyloxy)-3-undecyl-1,4-benzoquinone;
2,5-bis-(4-tertiarybutylphenylcarbonyloxy)-3-undecyl-1,4-benzoquinone;
2,5-bis-(2-fluorophenylcarbonyloxy)-3-undecyl-1,4-benzoquinone;

2,5-bis-(2-bromophenylcarbonyloxy)-3-undecyl-1,4-benzoquinone;
2,5-bis-(3-bromophenylcarbonyloxy)-3-undecyl-1,4-benzoquinone;
2,5-bis-(3-chlorophenylcarbonyloxy)-3-undecyl-1,4-benzoquinone;
2,5-bis-(2-chlorophenylcarbonyloxy)-3-undecyl-1,4-benzoquinone;
2,5-bis-(4-chlorophenylcarbonyloxy)-3-undecyl-1,4-benzoquinone;
2,5-bis-(4-bromophenylcarbonyloxy)-3-undecyl-1,4-benzoquinone;
2,5-bis-(3-nitrophenylcarbonyloxy)-3-undecyl-1,4-benzoquinone;
2,5-bis-(4-methylphenylcarbonyloxy)-3-undecyl-1,4-benzoquinone;
2,5-bis-(3-methylphenylcarbonyloxy)-3-undecyl-1,4-benzoquinone;
2,5-bis-(2-nitrophenylcarbonyloxy)-3-undecyl-1,4-benzoquinone;
2,5-bis-(phenylcarbonyloxy)-3-undecyl-1,4-benzoquinone;
2,5-bis-(4-fluorophenylcarbonyloxy)-3-undecyl-1,4-benzoquinone;
2,5-bis-(3-methoxyphenylcarbonyloxy)-3-undecyl-1,4-benzoquinone;
2,5-bis-(4-methoxyphenylcarbonyloxy)-3-undecyl-1,4-benzoquinone; and
2,5-bis-(2-iodophenylcarbonyloxy)-3-undecyl-1,4-benzoquinone; a prodrug thereof, all solvates and hydrates thereof and all salts thereof, in an amount sufficient for inhibiting or reducing activity of lipase.

10. A method of inhibiting lipase in a subject comprising administering the compound of claim 1.

11. A method of inhibiting plasma triglyceride levels postfeeding in a patient comprising administering the compound of claim 1.

12. A method of inhibiting LDL—Cholesterol uptake comprising administering the compound of claim 1.

* * * * *